United States Patent
Shinar et al.

(10) Patent No.: US 10,575,829 B2
(45) Date of Patent: Mar. 3, 2020

(54) MENSTRUAL STATE MONITORING

(71) Applicant: EarlySense Ltd., Ramat Gan (IL)

(72) Inventors: Zvika Shinar, Binyamina (IL); Guy Meger, Haifa (IL); Liat Tsoref, Tel Aviv (IL); Avner Halperin, Ramat Gan (IL)

(73) Assignee: EARLYSENSE LTD., Ramat Gran (IL)

( * ) Notice: Subject to any disclaimer, the term of this patent is extended or adjusted under 35 U.S.C. 154(b) by 0 days.

(21) Appl. No.: 14/726,706

(22) Filed: Jun. 1, 2015

(65) Prior Publication Data

US 2016/0058428 A1  Mar. 3, 2016

Related U.S. Application Data

(60) Provisional application No. 62/045,237, filed on Sep. 3, 2014, provisional application No. 62/057,250, filed on Sep. 30, 2014, provisional application No. 62/088,697, filed on Dec. 8, 2014, provisional application No. 62/102,031, filed on Jan. 11, 2015, provisional application No. 62/152,902, filed on Apr. 26, 2015.

(51) Int. Cl.

| | | |
|---|---|---|
| *G01N 33/48* | (2006.01) | |
| *A61B 10/00* | (2006.01) | |
| *A61B 5/00* | (2006.01) | |
| *A61B 5/0205* | (2006.01) | |
| *A61B 5/024* | (2006.01) | |
| *A61B 5/08* | (2006.01) | |

(52) U.S. Cl.
CPC ........ *A61B 10/0012* (2013.01); *A61B 5/0004* (2013.01); *A61B 5/0205* (2013.01); *A61B 5/4306* (2013.01); *A61B 5/4343* (2013.01); *A61B 5/486* (2013.01); *A61B 5/4806* (2013.01); *A61B 5/6891* (2013.01); *A61B 5/6892* (2013.01); *A61B 5/6893* (2013.01); *A61B 5/7267* (2013.01); *A61B 5/7275* (2013.01); *A61B 5/7278* (2013.01); *A61B 5/7282* (2013.01); *A61B 5/746* (2013.01); *A61B 5/02405* (2013.01); *A61B 5/0826* (2013.01); *A61B 2503/045* (2013.01); *A61B 2503/22* (2013.01); *A61B 2560/0487* (2013.01)

(58) Field of Classification Search
CPC ........ A61B 10/0012; A61B 2010/0016; A61B 2010/0019; A61B 2010/0029; A61B 5/72; A61B 5/02; A61B 5/01; G06F 19/34; G06F 19/345
See application file for complete search history.

(56) References Cited

U.S. PATENT DOCUMENTS

| | | |
|---|---|---|
| 4,465,077 A | 8/1984 | Schneider |
| 4,686,999 A | 8/1987 | Snyder |
| 4,832,038 A | 5/1989 | Arai |
| 5,169,234 A * | 12/1992 | Bohm ....................... G01J 5/10 356/43 |
| 5,253,656 A | 10/1993 | Rincoe |
| 5,479,939 A | 1/1996 | Ogino |
| 5,902,250 A | 5/1999 | Verrier |
| 5,964,720 A | 10/1999 | Pelz |
| 6,110,125 A | 8/2000 | Young et al. |
| 6,450,957 B1 | 9/2002 | Yoshimi |
| 6,547,743 B2 | 4/2003 | Brydon |
| 6,600,696 B1 * | 7/2003 | Lynn .............................. 368/23 |
| 6,719,708 B1 | 4/2004 | Jansen |
| 7,077,810 B2 | 7/2006 | Lange |
| 7,314,451 B2 | 1/2008 | Halperin |
| 7,351,206 B2 | 4/2008 | Suzuki |
| 7,572,225 B2 | 8/2009 | Stahmann |
| 7,610,094 B2 | 10/2009 | Stahmann |
| 8,376,954 B2 | 2/2013 | Lange |
| 8,403,865 B2 | 3/2013 | Halperin |
| 8,430,561 B2 * | 4/2013 | Agronin ..................... G01J 5/02 374/121 |
| 8,491,492 B2 | 7/2013 | Shinar |
| 8,517,953 B2 | 8/2013 | Lange |
| 8,585,607 B2 | 11/2013 | Klap |

(Continued)

FOREIGN PATENT DOCUMENTS

| | | | |
|---|---|---|---|
| EP | 0132119 A2 * | 1/1985 | ............. A61B 5/024 |
| JP | 2001-145605 | 5/2001 | |

(Continued)

OTHER PUBLICATIONS

Yildirir, A. et al "Effects of menstrual cycle on cardiac autonomic Innervation as assessed by heart rate variability"; A.A. E. 2002; 7(1):60-63.*

Vallejo, M. et al "Age, body mass index, and menstrual cycle influence young women's heart rate variability. A multivariate analysis"; Clin Auton Res (2005) 15:292-298.*

(Continued)

*Primary Examiner* — Anna Skibinsky

(74) *Attorney, Agent, or Firm* — Roach Brown McCarthy & Gruber, P.C.; Kevin D. McCarthy

(57) ABSTRACT

Apparatus and methods are described for monitoring a female subject. A sensor is configured to monitor the subject without contacting the subject or clothes the subject is wearing, and without viewing the subject or clothes the subject is wearing, and to generate a sensor signal in response to the monitoring. A computer processor is configured to receive the sensor signal, and to analyze the sensor signal. In response to the analyzing, the computer processor is configured to automatically identify a menstrual state of the subject, and to generate an output in response thereto. Other applications are also described.

23 Claims, 5 Drawing Sheets

(56) References Cited

U.S. PATENT DOCUMENTS

| | | | |
|---|---|---|---|
| 8,603,010 B2 | 12/2013 | Lange | |
| 8,679,030 B2 | 3/2014 | Shinar | |
| 8,679,034 B2 | 3/2014 | Halperin | |
| 8,731,646 B2 | 5/2014 | Halperin | |
| 8,734,360 B2 | 5/2014 | Klap | |
| 8,821,418 B2 | 9/2014 | Meger | |
| 8,840,564 B2 | 9/2014 | Pinhas | |
| 8,882,684 B2 | 11/2014 | Halperin | |
| 8,942,779 B2 | 1/2015 | Halperin | |
| 8,992,434 B2 | 3/2015 | Halperin | |
| 8,998,830 B2 | 4/2015 | Halperin | |
| 9,026,199 B2 | 5/2015 | Halperin | |
| 2002/0196148 A1 | 12/2002 | Nunome | |
| 2003/0144829 A1 | 7/2003 | Geatz | |
| 2004/0010202 A1 | 1/2004 | Nakatani | |
| 2004/0030531 A1* | 2/2004 | Miller | A61B 5/0002 702/182 |
| 2004/0111045 A1 | 6/2004 | Sullivan | |
| 2004/0193069 A1* | 9/2004 | Takehara | 600/551 |
| 2004/0210155 A1 | 10/2004 | Takemura | |
| 2005/0080349 A1 | 4/2005 | Okada | |
| 2006/0129047 A1 | 6/2006 | Ruotoistenmaki | |
| 2007/0118054 A1 | 5/2007 | Pinhas | |
| 2007/0149883 A1* | 6/2007 | Yesha | A61B 5/1102 600/485 |
| 2007/0299910 A1 | 12/2007 | Fontenot | |
| 2008/0033304 A1 | 2/2008 | Dalal | |
| 2008/0275349 A1 | 11/2008 | Halperin | |
| 2009/0203972 A1* | 8/2009 | Heneghan et al. | 600/301 |
| 2009/0234200 A1 | 9/2009 | Husheer | |
| 2012/0108989 A1 | 5/2012 | Gargiulo | |
| 2012/0132211 A1 | 5/2012 | Halperin | |
| 2012/0253142 A1 | 10/2012 | Meger | |
| 2012/0253206 A1* | 10/2012 | Fukuda et al. | 600/483 |
| 2013/0006124 A1* | 1/2013 | Eyal | A61B 5/024 600/483 |
| 2013/0018626 A1* | 1/2013 | Chi | G01J 5/0003 702/135 |
| 2013/0137940 A1* | 5/2013 | Schafer | 600/301 |
| 2013/0174345 A1 | 7/2013 | Leu | |
| 2013/0245389 A1 | 9/2013 | Schultz | |
| 2013/0245502 A1 | 9/2013 | Lange | |
| 2014/0005502 A1 | 1/2014 | Klap | |
| 2014/0057232 A1* | 2/2014 | Wetmore | G09B 19/00 434/236 |
| 2014/0073486 A1* | 3/2014 | Ahmed | A61B 5/02405 482/9 |
| 2014/0371635 A1 | 12/2014 | Shinar | |
| 2015/0119749 A1 | 4/2015 | Graf et al. | |
| 2015/0164433 A1 | 6/2015 | Halperin | |
| 2015/0164438 A1 | 6/2015 | Halperin | |
| 2015/0190087 A1 | 7/2015 | Shinar | |
| 2016/0058429 A1 | 3/2016 | Shinar | |
| 2016/0174946 A1 | 6/2016 | Sacks et al. | |
| 2019/0083044 A1 | 3/2019 | Halperin | |
| 2019/0090860 A1 | 3/2019 | Shinar | |

FOREIGN PATENT DOCUMENTS

| | | | |
|---|---|---|---|
| JP | 2001-258855 | 9/2001 | |
| JP | 2004-049388 | 2/2004 | |
| JP | 2004-049838 | 2/2004 | |
| WO | 96/008197 | 3/1996 | |
| WO | 97/040748 | 11/1997 | |
| WO | 03/013355 | 2/2003 | |
| WO | 2007/052108 | 5/2007 | |
| WO | 2015/008285 | 1/2015 | |
| WO | WO 2015150434 A1 * | 10/2015 | A61B 10/0012 |
| WO | WO-2016131630 A1 * | 8/2016 | A61B 10/0012 |
| WO | 2019/053719 A1 | 3/2019 | |

OTHER PUBLICATIONS

Bai X, et al; "Influence of the menstrual cycle on nonlinear properties of heart rate variability in young women". Am J Physiol Heart Circ Physiol 297: H765-H774, 2009.*

Seebauer, M. et al; "Changes of respiratory sinus arrhythmia during the menstrual cycle depend on average heart rate", Eur J Appl Physiol (2002) 87: 309-314.*

Leicht, A. S. et al; "Heart rate variability and endogenous sex hormones during the menstrual cycle in young women"; Experimental Physiology (2003) 88.3, 441-446.*

Sato, N. et. al; "Power Spectral Analysis of Heart Rate Variability in Healthy Young Women During the Normal Menstrual Cycle", Psychosomatic Medicine 57:331-335 (1995).*

Princi, T. et al; "Parametric evaluation of heart rate variability during the menstrual cycle in young women"; Biomedical Sciences Instrumentation; No. 41, p. 340-345 (2005).*

Boudreau, P. et.al; "Circadian variation of Herat Rate Variability Across Sleep Stages"; Sleep, vol. 36 No. 12, 2013; p. 1919-1928.*

Elsenbruch, S. et.al; "Heart rate variability during waking and Sleep in Healthy Males and Females"; Sleep, vol. 22, No. 8, 1999; p. 1067-1071.*

Shechter, A et.al; "Circadian variation of sleep during the follicular and Luteal Phases of the Menstrual Cycle"; Sleep, vol. 33, No. 5, 2010; p. 647-656.*

Shechter, A et.al; "Sleep, Hormones, and Circadian Rhythms throughout the Menstrual Cycle in Healthy Women and Women with Premenstrual Dysphoric Disorder"; International Journal of Endocrinology, vol. 2010; 2010; p. 1-17.*

Baker, F. et al; "Circadian rhythms, sleep, and the menstrual cycle"; Sleep Medicine 8 (2007) 613-622.*

Vallejo, M. et. al; "Age, body mass index, and menstrual cycle influence young women's heart rate variability. A multivariable analysis" Clin Auton Res (2005) 15: 292-298.*

Shinar, Z. et al; "Automatic Detection of Slow-Wave-Sleep Using Heart Rate Variability"; Computers in Cardiology 2001; 28:593-596.*

Tenan, M. S. et al; "Changes in resting heart rate variability across the menstrual cycle"; Psychophysiology, 51 (2014), 996-1004.*

Driver, H. S. et al; "Sleep and the Sleep Electroencephalogram across the Menstrual Cycle in Young Healthy Women"; Journal of Clinical Endocrinology and Metabolism, vol. 81; No. 2; p. 728-735.*

Driver, H. S. et al; "Sleep and the sleep electroencephalogram across the menstrual cycle in young healthy women," Journal of Clinical Endocrinology and Metabolism, vol. 81, No. 2, pp. 728-735, 1996.*

Alihanka, J. et al., "A static charge sensitive bed. A new method for recording body movement during sleep", Electroencephalography and Clinical Neurophysiology 1979; 46(6): 731-4.

Tamura T. et al., "A system for monitoring temperature distribution in bed and its application to the assessment of body movement", Physiological Measurement, Institute of Physics Publishing, Bristol, GB 1993; 14(1): 33-41.

Stein et al., (1999) Changes in 24-hour heart rate variability during normal pregnancy. Am J Obstet Gynecol 180(4): 978-85.

Notice of References Cited from U.S. Appl. No. 14/843,021, dated Jan. 22, 2016, 1 page.

* cited by examiner

MENSTRUAL STATE MONITORING

CROSS-REFERENCE TO RELATED APPLICATIONS

The present application claims the benefit of (i) U.S. Provisional Application 62/045,237, entitled "Monitoring a Sleeping Subject," filed Sep. 3, 2014, (ii) U.S. Provisional Application 62/057,250, entitled "Monitoring a Sleeping Subject," filed Sep. 30, 2014, (iii) U.S. Provisional Application 62/088,697, entitled "Monitoring a Sleeping Subject," filed Dec. 8, 2014, (iv) U.S. Provisional Application 62/102,031, entitled "Monitoring a Sleeping Subject," filed Jan. 11, 2015, and (v) U.S. Pat. No. 62/152,902, filed Apr. 26, 2015, entitled "Monitoring a Sleeping Subject."

Each of the above applications is incorporated herein by reference.

FIELD OF EMBODIMENTS OF THE INVENTION

The present invention relates generally to monitoring a female subject in her bed, typically in a home setting. Specifically, some applications of the present invention relate to automatically identifying a state of a female subject's menstrual cycle, and/or whether the female subject is in a pregnant or non-pregnant state.

BACKGROUND

There is great variation in the lengths of women's menstrual cycles. It is often the case that women would like to know the current phase of their menstrual cycle. Of particular interest to many is knowledge of when they are in the "fertile window" which occurs from approximately five days before ovulation until two days after ovulation. Typically, urine tests, calendar-based methods, and symptoms-based methods (in which parameters such as cervical mucus, cervical position, and basal body temperature are measured) are used for such determinations.

SUMMARY OF EMBODIMENTS

In accordance with some applications of the present invention, a sensor monitors a female subject and generates a sensor signal in response to the monitoring. A computer processor receives the sensor signal and, in response to analyzing the sensor signal, automatically identifies a menstrual state of the subject, and/or a pregnancy state of the subject (i.e., whether the subject is in a pregnant or a non-pregnant state). For example, the computer processor may identify an aspect of the sensor signal, such as a cardiac-related aspect of the sensor signal, and/or a respiration-related aspect of the sensor signal, and may perform the identification of the subject's state in response thereto. In response to determining the subject's menstrual state, and/or pregnancy state, the computer processor generates an output.

Typically, the sensor performs monitoring of the subject without contacting the subject or clothes the subject is wearing, and/or without viewing the subject or clothes the subject is wearing. For example, the sensor may perform the monitoring without having a direct line of sight of the subject's body, or the clothes that the subject is wearing. Further typically, the sensor performs monitoring of the subject without requiring subject compliance (i.e., without the subject needing to perform an action to facilitate the monitoring that would not have otherwise been performed).

It is noted that, prior to the monitoring, certain actions (such as purchasing the sensor and placing the sensor under the subject's bed) may need to be performed by the subject. The term "without requiring subject compliance" should not be interpreted as excluding such actions. Rather the term "without requiring subject compliance" should be interpreted as meaning that, once the sensor has been purchased, placed in a suitable position and activated, the sensor can be used to monitor the subject (e.g., to monitor the subject during repeated monitoring sessions), without the subject needing to perform any actions to facilitate the monitoring that would not have otherwise been performed.

Typically, the sensor is disposed on or within the subject's bed, and configured to monitor the subject automatically, while she is in her bed. For example, the sensor may be disposed underneath the subject's mattress such that the subject is monitored while she is lying upon the mattress, and while carrying out her normal sleeping routine, without the subject needing to perform an action to facilitate the monitoring that would not have otherwise been performed.

Typically, the sensor is a non-temperature sensor (i.e., the sensor is not configured to measure a temperature of the subject), and the computer processor is configured to identify the subject's menstrual state and/or pregnancy state without determining a temperature of the subject.

In response to determining the subject's menstrual state and/or pregnancy state, the computer processor generates an output. For example, the computer processor may drive an output device (e.g., a monitor, or the screen of a tablet device or a smartphone) to display (or otherwise output) an output that is indicative of the identified menstrual state and/or pregnancy state. Alternatively or additionally, the processor may drive an output device (e.g., a monitor, or the screen of a tablet device or a smartphone) to display (or otherwise output) an output that is indicative of a recommended action to be taken by the user (e.g., "intercourse is recommended within the next 48 hours"), based upon the identified menstrual state and/or pregnancy state. Alternatively or additionally, the processor may drive a device (such as a room-climate-regulation device) in the subject's bedroom to perform a function or to change a parameter of its functioning in response to the identified menstrual state and/or pregnancy state.

There is therefore provided, in accordance with some applications of the present invention, apparatus for monitoring a female subject, the apparatus including:

a sensor, configured to monitor the subject without contacting the subject or clothes the subject is wearing, and without viewing the subject or clothes the subject is wearing, and to generate a sensor signal in response to the monitoring; and a computer processor, configured to:
  receive the sensor signal,
  analyze the sensor signal,
  in response to the analyzing, automatically identify a menstrual state of the subject, and
  generate an output in response thereto.

For some applications, the computer processor is configured to identify the subject's menstrual state without determining a temperature of the subject.

For some applications, the sensor is not configured to measure a temperature of the subject.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the sensor is configured to be disposed upon or within a bed of the subject, and is configured to monitor the subject automatically while the subject is in her bed.

For some applications, the computer processor is configured to identify the menstrual state of the subject, using a machine-learning algorithm.

For some applications, the sensor is configured to monitor the subject without requiring compliance of the subject.

For some applications, the output includes a control signal to a room-climate-regulation device, and the computer processor is configured to generate the output by communicating the control signal to the room-climate-regulation device in response to the identified menstrual state.

For some applications, the computer processor is further configured, in response to identifying the subject's menstrual state, to identify that the subject is likely to experience premenstrual syndrome (PMS) in more than 0.5 days, the computer processor being configured to generate the output in response thereto.

For some applications, the computer processor is configured to identify the menstrual state of the subject by identifying that the subject is likely to ovulate in less than 10 days.

For some applications, the computer processor is configured to identify the menstrual state of the subject by identifying that the subject is likely to ovulate in less than five days.

For some applications, the computer processor is configured to identify the menstrual state of the subject by identifying that the subject is likely to ovulate in more than 0.5 days.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to ovulate in less than 10 days by:
at least once, prior to currently receiving the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning an ovulation-prediction rule, and
using the ovulation-prediction rule to identify that the subject is likely to ovulate in less than 10 days, based upon the currently-received sensor signal.

For some applications:
the computer processor is further configured, in response to identifying the menstrual state of the subject, to identify that the subject is likely to experience premenstrual syndrome (PMS) in less than three days,
the computer processor being configured to generate the output in response thereto.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to experience PMS in less than three days by:
at least once, prior to currently receiving the sensor signal:
receiving, via the input unit, an input that is indicative of an occurrence of PMS of the subject, and
identifying an aspect of the sensor signal at a time at which the input was received,
in response to the input and the identified aspect of the sensor signal, learning a PMS-prediction rule, and
using the PMS-prediction rule to identify that the subject is likely to experience PMS in less than three days, based upon the currently-received sensor signal.

For some applications, the computer processor is configured:
in response to the analyzing, to identify an aspect of the sensor signal selected from the group consisting of: a cardiac-related aspect of the sensor signal, and a respiration-related aspect of the sensor signal, and
to identify the menstrual state of the subject, in response to the identified aspect.

For some applications, the identified aspect of the sensor signal includes a respiratory rate of the subject, and the computer processor is configured to identify the menstrual state of the subject by comparing the identified respiratory rate to a baseline respiratory rate.

For some applications:
the apparatus further includes an input unit,
the identified aspect of the sensor signal is a currently-identified aspect of the sensor signal, and
the computer processor is configured to identify the current phase of the menstrual cycle by:
at least once, prior to the identification of the currently-identified aspect of the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning a phase-identification rule, and
using the phase-identification rule to identify the menstrual state of the subject.

For some applications, the identified aspect of the sensor signal includes a heart rate variability (HRV) signal, the computer processor being configured to identify the menstrual state in response to the HRV signal.

For some applications, in response to the HRV signal, the computer processor is configured to identify that the current phase of the subject's menstrual cycle is a late follicular phase.

For some applications, the computer processor is configured to identify that the current phase of the subject's menstrual cycle is the late follicular phase in response to an aspect of a component of a power spectrum of the HRV signal.

For some applications, the computer processor is configured to identify that the current phase of the subject's menstrual cycle is the late follicular phase by identifying that the component of the power spectrum of the HRV signal has an amplitude that exceeds a threshold.

For some applications, the component of the power spectrum of the HRV signal lies between 0.1 and 0.5 Hz, the computer processor being configured to identify that the current phase of the subject's menstrual cycle is the late follicular phase in response to an aspect of the component of the power spectrum.

For some applications, the identified aspect of the sensor signal includes a heart rate of the subject, and the computer processor is configured to identify the menstrual state of the subject by comparing the identified heart rate to a baseline heart rate.

For some applications, the computer processor is configured, in response to the comparing, to:

ascertain that the identified heart rate is greater than the baseline heart rate; and in response thereto, identify the menstrual state of the subject by identifying that the subject is currently within a given amount of time of ovulation of the subject.

For some applications, the computer processor is configured to identify that the subject is currently within the given amount of time of ovulation of the subject by identifying that less than the given amount of time has transpired since the subject ovulated.

For some applications, the computer processor is configured, in response to ascertaining that the identified heart rate is greater than the baseline heart rate, to identify that the subject is currently within less than two days of ovulation of the subject.

For some applications, the computer processor is configured to identify that the subject is currently within the given amount of time of ovulation of the subject in response to the identified heart rate being less than five heartbeats-per-minute greater than the baseline heart rate.

For some applications, the sensor is configured to monitor the subject during a sleeping session of the subject.

For some applications:

the computer processor is configured to analyze the sensor signal by identifying an aspect of the sensor signal that is exhibited at least two hours from a beginning of the sleeping session, and the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

For some applications:

the computer processor is further configured, in response to analyzing the sensor signal, to determine a level of motion of the subject, the computer processor is configured to analyze the sensor signal by identifying an aspect of the sensor signal that is exhibited while the level of motion does not exceed a threshold, and the computer processor is configured to identify the menstrual state of the subject (i) in response to the aspect of the sensor signal that is exhibited while the level of motion does not exceed the threshold, and (ii) substantially not in response to any aspect of the sensor signal that is exhibited while the level of motion exceeds the threshold.

For some applications:

the computer processor is further configured, in response to analyzing the sensor signal, to identify a sleep stage of the subject during the sleeping session, the computer processor is configured to analyze the sensor signal by identifying an aspect of the sensor signal that is exhibited while the identified sleep stage is a particular sleep stage, and the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

For some applications, the particular sleep stage is a slow-wave sleep stage.

For some applications, the particular sleep stage is a rapid-eye-movement sleep stage.

For some applications, the identified aspect of the sensor signal includes a heart rate variability (HRV) signal, the computer processor being configured to identify the menstrual state of the subject in response to the HRV signal that is exhibited while the identified sleep stage is the particular sleep stage.

For some applications:

the computer processor is further configured, in response to analyzing the sensor signal, to identify an end of a chronologically-first sleep cycle of the subject during the sleeping session, the computer processor is configured to analyze the sensor signal by identifying an aspect of the sensor signal that is exhibited following the end of the chronologically-first sleep cycle, and the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

For some applications:

the computer processor is further configured, in response to analyzing the sensor signal, to identify an end of a chronologically-second sleep cycle of the subject during the sleeping session, the computer processor is configured to analyze the sensor signal by identifying an aspect of the sensor signal that is exhibited following the end of the chronologically-second sleep cycle, and the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

There is further provided, in accordance with some applications of the present invention, apparatus for monitoring a female subject and for use with a bed, the apparatus including:

a sensor configured to be disposed upon or within the bed, to automatically monitor the subject while the subject is in the bed, and to generate a sensor signal in response to the monitoring; and a computer processor, configured to:
receive the sensor signal,
analyze the sensor signal,
in response to the analyzing, automatically identify a menstrual state of the subject, and
generate an output in response thereto.

For some applications, the bed includes a mattress, and the sensor is configured to be disposed underneath the mattress and to automatically monitor the subject while the subject is lying upon the mattress.

For some applications, the computer processor is configured to identify the subject's menstrual state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the computer processor is configured to identify the menstrual state of the subject, using a machine-learning algorithm.

For some applications, the sensor is configured to monitor the subject without contacting the subject or clothes the subject is wearing, and without viewing the subject or clothes the subject is wearing.

For some applications, the sensor is configured to monitor the subject without requiring compliance of the subject.

For some applications, the output includes a control signal to a room-climate-regulation device, and the computer processor is configured to generate the output by communicating the control signal to the room-climate-regulation device in response to the identified menstrual state.

For some applications, the computer processor is further configured, in response to identifying the subject's menstrual state, to identify that the subject is likely to experience premenstrual syndrome (PMS) in more than 0.5 days, the computer processor being configured to generate the output in response thereto.

For some applications, the computer processor is configured to identify the menstrual state of the subject by identifying that the subject is likely to ovulate in less than 10 days.

For some applications, the computer processor is configured to identify the menstrual state of the subject by identifying that the subject is likely to ovulate in less than five days.

For some applications, the computer processor is configured to identify the menstrual state of the subject by identifying that the subject is likely to ovulate in more than 0.5 days.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to ovulate in less than 10 days by:
at least once, prior to currently receiving the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning an ovulation-prediction rule, and
using the ovulation-prediction rule to identify that the subject is likely to ovulate in less than 10 days, based upon the currently-received sensor signal.

For some applications:
the computer processor is further configured, in response to identifying the menstrual state of the subject, to identify that the subject is likely to experience premenstrual syndrome (PMS) in less than three days, the computer processor being configured to generate the output in response thereto.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to experience PMS in less than three days by:
at least once, prior to currently receiving the sensor signal:
receiving, via the input unit, an input that is indicative of an occurrence of PMS of the subject, and
identifying an aspect of the sensor signal at a time at which the input was received,
in response to the input and the identified aspect of the sensor signal, learning a PMS-prediction rule, and
using the PMS-prediction rule to identify that the subject is likely to experience PMS in less than three days, based upon the currently-received sensor signal.

For some applications, the computer processor is configured:
in response to the analyzing, to identify an aspect of the sensor signal selected from the group consisting of: a cardiac-related aspect of the sensor signal, and a respiration-related aspect of the sensor signal, and
to identify the menstrual state of the subject, in response to the identified aspect.

For some applications, the identified aspect of the sensor signal includes a respiratory rate of the subject, and the computer processor is configured to identify the menstrual state of the subject by comparing the identified respiratory rate to a baseline respiratory rate.

For some applications:
the apparatus further includes an input unit,
the identified aspect of the sensor signal is a currently-identified aspect of the sensor signal, and
the computer processor is configured to identify the current phase of the menstrual cycle by:
at least once, prior to the identification of the currently-identified aspect of the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning a phase-identification rule, and
using the phase-identification rule to identify the menstrual state of the subject.

For some applications, the identified aspect of the sensor signal includes a heart rate variability (HRV) signal, the computer processor being configured to identify the menstrual state in response to the HRV signal.

For some applications, in response to the HRV signal, the computer processor is configured to identify that the current phase of the subject's menstrual cycle is a late follicular phase.

For some applications, the computer processor is configured to identify that the current phase of the subject's menstrual cycle is the late follicular phase in response to an aspect of a component of a power spectrum of the HRV signal.

For some applications, the computer processor is configured to identify that the current phase of the subject's menstrual cycle is the late follicular phase by identifying that the component of the power spectrum of the HRV signal has an amplitude that exceeds a threshold.

For some applications, the component of the power spectrum of the HRV signal lies between 0.1 and 0.5 Hz, the computer processor being configured to identify that the current phase of the subject's menstrual cycle is the late follicular phase in response to an aspect of the component of the power spectrum.

For some applications, the identified aspect of the sensor signal includes a heart rate of the subject, and the computer processor is configured to identify the menstrual state of the subject by comparing the identified heart rate to a baseline heart rate.

For some applications, the computer processor is configured, in response to the comparing, to:

ascertain that the identified heart rate is greater than the baseline heart rate; and in response thereto, identify the menstrual state of the subject by identifying that the subject is currently within a given amount of time of ovulation of the subject.

For some applications, the computer processor is configured to identify that the subject is currently within the given amount of time of ovulation of the subject by identifying that less than the given amount of time has transpired since the subject ovulated.

For some applications, the computer processor is configured, in response to ascertaining that the identified heart rate is greater than the baseline heart rate, to identify that the subject is currently within less than two days of ovulation of the subject.

For some applications, the computer processor is configured to identify that the subject is currently within the given amount of time of ovulation of the subject in response to the identified heart rate being less than five heartbeats-per-minute greater than the baseline heart rate.

For some applications, the sensor is configured to monitor the subject during a sleeping session of the subject.

For some applications:

the computer processor is configured to analyze the sensor signal by identifying an aspect of the sensor signal that is exhibited at least two hours from a beginning of the sleeping session, and the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

For some applications:

the computer processor is further configured, in response to analyzing the sensor signal, to determine a level of motion of the subject, the computer processor is configured to analyze the sensor signal by identifying an aspect of the sensor signal that is exhibited while the level of motion does not exceed a threshold, and the computer processor is configured to identify the menstrual state of the subject (i) in response to the aspect of the sensor signal that is exhibited while the level of motion does not exceed the threshold, and (ii) substantially not in response to any aspect of the sensor signal that is exhibited while the level of motion exceeds the threshold.

For some applications:

the computer processor is further configured, in response to analyzing the sensor signal, to identify a sleep stage of the subject during the sleeping session, the computer processor is configured to analyze the sensor signal by identifying an aspect of the sensor signal that is exhibited while the identified sleep stage is a particular sleep stage, and the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

For some applications, the particular sleep stage is a slow-wave sleep stage.

For some applications, the particular sleep stage is a rapid-eye-movement sleep stage.

For some applications, the identified aspect of the sensor signal includes a heart rate variability (HRV) signal, the computer processor being configured to identify the menstrual state of the subject in response to the HRV signal that is exhibited while the identified sleep stage is the particular sleep stage.

For some applications:

the computer processor is further configured, in response to analyzing the sensor signal, to identify an end of a chronologically-first sleep cycle of the subject during the sleeping session, the computer processor is configured to analyze the sensor signal by identifying an aspect of the sensor signal that is exhibited following the end of the chronologically-first sleep cycle, and the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

For some applications:

the computer processor is further configured, in response to analyzing the sensor signal, to identify an end of a chronologically-second sleep cycle of the subject during the sleeping session, the computer processor is configured to analyze the sensor signal by identifying an aspect of the sensor signal that is exhibited following the end of the chronologically-second sleep cycle, and the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

There is additionally provided, in accordance with some applications of the present invention, apparatus for monitoring a female subject, the apparatus including:

a sensor, configured to monitor the subject and to generate a sensor signal in response to the monitoring; and a computer processor, configured to:

receive the sensor signal, derive a cardiac-related aspect of the sensor signal by analyzing the sensor signal, based upon the derived cardiac-related aspect of the sensor signal, automatically identify a menstrual state of the subject, and generate an output in response thereto.

For some applications, the computer processor is configured to identify the subject's menstrual state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the sensor is configured to monitor the subject without requiring compliance of the subject.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the sensor is configured to be disposed upon or within a bed of the subject, and is configured to monitor the subject automatically while the subject is in her bed.

For some applications, the computer processor is configured to identify the menstrual state of the subject, using a machine-learning algorithm.

For some applications, the sensor is configured to monitor the subject without contacting the subject or clothes the subject is wearing, and without viewing the subject or clothes the subject is wearing.

For some applications, the output includes a control signal to a room-climate-regulation device, and the computer processor is configured to generate the output by communicating the control signal to the room-climate-regulation device in response to the identified menstrual state.

For some applications, the computer processor is further configured, in response to identifying the subject's menstrual state, to identify that the subject is likely to experience premenstrual syndrome (PMS) in more than 0.5 days, the computer processor being configured to generate the output in response thereto.

For some applications:

the apparatus further includes an input unit, and the computer processor is configured to identify menstrual state of the subject by:

at least once, prior to currently receiving the sensor signal:
receiving, via the input unit, an input that is indicative of a phase of the subject's menstrual cycle, and
identifying an aspect of the sensor signal at a time at which the input was received, in response to the input and the identified aspect of the sensor signal, learning a phase-identification rule, and using the phase-identification rule to identify a current phase of the subject's menstrual cycle, based upon the currently-received sensor signal.

For some applications, the computer processor is configured to identify the menstrual state of the subject by identifying that the subject is likely to ovulate in less than 10 days.

For some applications, the computer processor is configured to identify the menstrual state of the subject by identifying that the subject is likely to ovulate in less than five days.

For some applications, the computer processor is configured to identify the menstrual state of the subject by identifying that the subject is likely to ovulate in more than 0.5 days.

For some applications, the computer processor is configured to derive a heart rate variability (HRV) signal from the sensor signal, and to identify the subject's menstrual state, in response thereto.

For some applications:

the apparatus further includes an input unit, and the computer processor is configured to identify that the subject is likely to ovulate in less than 10 days by:

at least once, prior to currently receiving the sensor signal:
receiving, via the input unit, an input that is indicative of a phase of the subject's menstrual cycle, and
identifying an aspect of the sensor signal at a time at which the input was received, in response to the input and the identified aspect of the sensor signal, learning an ovulation-prediction rule, and using the ovulation-prediction rule to identify that the subject is likely to ovulate in less than 10 days, based upon the currently-received sensor signal.

For some applications:

the computer processor is further configured, in response to identifying the menstrual state of the subject, to identify that the subject is likely to experience premenstrual syndrome (PMS) in less than three days, the computer processor being configured to generate the output in response thereto.

For some applications, the computer processor is configured to derive a heart rate variability (HRV) signal from the sensor signal, and to identify the subject's menstrual state, in response thereto.

For some applications:

the apparatus further includes an input unit, and the computer processor is configured to identify that the subject is likely to experience PMS in less than three days by:

at least once, prior to currently receiving the sensor signal:
receiving, via the input unit, an input that is indicative of an occurrence of PMS of the subject, and
identifying an aspect of the sensor signal at a time at which the input was received, in response to the input and the identified aspect of the sensor signal, learning a PMS-prediction rule, and using the PMS-prediction rule to identify that the subject is likely to experience PMS in less than three days, based upon the currently-received sensor signal.

For some applications, the cardiac-related aspect of the sensor signal includes a heart rate variability (HRV) signal, the computer processor being configured to identify the menstrual state of the subject in response to the HRV signal.

For some applications, in response to the HRV signal, the computer processor is configured to identify that a current phase of the subject's menstrual cycle is a late follicular phase.

For some applications, the computer processor is configured to identify that the current phase of the subject's menstrual cycle is the late follicular phase in response to an aspect of a component of a power spectrum of the HRV signal.

For some applications, the computer processor is configured to identify that the current phase of the subject's menstrual cycle is the late follicular phase by identifying that the component of the power spectrum of the HRV signal has an amplitude that exceeds a threshold.

For some applications, the component of the power spectrum of the HRV signal lies between 0.1 and 0.5 Hz, the computer processor being configured to identify that the current phase of the subject's menstrual cycle is the late follicular phase in response to an aspect of the component of the power spectrum.

For some applications, the cardiac-related aspect of the sensor signal includes a heart rate of the subject, and the computer processor is configured to identify a current phase of the menstrual cycle of the subject by comparing the derived heart rate to a baseline heart rate.

For some applications, the computer processor is configured, in response to the comparing, to:

ascertain that the derived heart rate is greater than the baseline heart rate; and in response thereto, identify the current phase of the menstrual cycle of the subject by identifying that the subject is currently within a given amount of time of ovulation of the subject.

For some applications, the computer processor is configured to identify that the subject is currently within the given amount of time of ovulation of the subject by identifying that less than the given amount of time has transpired since the subject ovulated.

For some applications, the computer processor is configured, in response to ascertaining that the identified heart rate is greater than the baseline heart rate, to identify that the subject is currently within less than two days of ovulation of the subject.

For some applications, the computer processor is configured to identify that the subject is currently within the given amount of time of ovulation of the subject in response to the derived heart rate being less than five heartbeats-per-minute greater than the baseline heart rate.

For some applications, the sensor is configured to monitor the subject during a sleeping session of the subject.

For some applications:

the computer processor is configured to derive the cardiac-related aspect of the sensor signal by identifying an aspect of the sensor signal that is exhibited at least two hours from a beginning of the sleeping session, and the computer processor is configured to identify the menstrual state of the subject (i) in response to the cardiac-related aspect of the sensor signal that is exhibited at least two hours from the beginning of the sleeping session, and (ii) substantially not in response to any aspect of the sensor signal that is exhibited less than two hours from the beginning of the sleeping session.

For some applications:

the computer processor is further configured, in response to analyzing the sensor signal, to determine a level of motion of the subject, the computer processor is configured to derive the cardiac-related aspect of the sensor signal by deriving the cardiac-related aspect of the sensor signal that is exhibited while the level of motion does not exceed a threshold, and the computer processor is configured to identify the menstrual state of the subject (i) in response to the cardiac-related aspect of the sensor signal that is exhibited while the level of motion does not exceed the threshold, and (ii) substantially not in response to any aspect of the sensor signal that is exhibited while the level of motion exceeds the threshold.

For some applications:

the computer processor is further configured, in response to analyzing the sensor signal, to identify a sleep stage of the subject during the sleeping session, the computer processor is configured to derive the cardiac-related aspect of the sensor signal by deriving a cardiac-related aspect of the sensor signal that is exhibited while the identified sleep stage is a particular sleep stage, and the computer processor is configured to identify the menstrual state of the subject (i) in response to the cardiac-related aspect of the sensor signal that is exhibited while the identified sleep stage is the particular sleep stage, and (ii) substantially not in response to any aspect of the sensor signal that is exhibited while the identified sleep stage is not the particular sleep stage.

For some applications, the particular sleep stage is a slow-wave sleep stage.

For some applications, the particular sleep stage is a rapid-eye-movement sleep stage.

For some applications, the cardiac-related aspect of the sensor signal includes a heart rate variability (HRV) signal, the computer processor being configured to identify the current phase of the menstrual cycle of the subject in response to the HRV signal that is exhibited while the identified sleep stage is the particular sleep stage.

For some applications:

the computer processor is further configured, in response to analyzing the sensor signal, to identify an end of a chronologically-first sleep cycle of the subject during the sleeping session, the computer processor is configured to derive the cardiac-related aspect of the sensor signal by deriving a cardiac-related aspect of the sensor signal that is exhibited following the end of the chronologically-first sleep cycle, and the computer processor is configured to identify the menstrual state of the subject (i) in response to the cardiac-related aspect of the sensor signal that is exhibited following the end of the chronologically-first sleep cycle, and (ii) substantially not in response to any aspect of the sensor signal that is exhibited before the end of the chronologically-first sleep cycle.

For some applications:

the computer processor is further configured, in response to analyzing the sensor signal, to identify an end of a chronologically-second sleep cycle of the subject during the sleeping session, the computer processor is configured to derive the cardiac-related aspect of the sensor signal by deriving a cardiac-related aspect of the sensor signal that is exhibited following the end of the chronologically-second sleep cycle, and the computer processor is configured to identify the menstrual state of the subject (i) in response to the cardiac-related aspect of the sensor signal that is exhibited following the end of the chronologically-second sleep cycle, and (ii) substantially not in response to any aspect of the sensor signal that is exhibited before the end of the chronologically-second sleep cycle.

There is further provided, in accordance with some applications of the present invention, apparatus for monitoring a female subject, the apparatus including:

a sensor, configured to monitor the subject without requiring compliance of the subject, and to generate a sensor signal in response to the monitoring; and a computer processor, configured to:
receive the sensor signal,
analyze the sensor signal,
in response to the analyzing, automatically identify whether the subject is in a pregnant state or a non-pregnant state, and
generate an output in response thereto.

For some applications, the computer processor is configured to identify whether the subject is in the pregnant state or the non-pregnant state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the sensor is configured to be disposed upon or within a bed of the subject, and is configured to monitor the subject automatically while the subject is in her bed.

For some applications, the sensor is configured to monitor the subject without contacting the subject or clothes the subject is wearing, and without viewing the subject or clothes the subject is wearing.

For some applications, the output includes a control signal to a room-climate-regulation device, and the computer processor is configured to generate the output by communicating the control signal to the room-climate-regulation device in response to the identified state.

For some applications, the computer processor is configured to identify whether the subject is in the pregnant state or the non-pregnant state, using a machine-learning algorithm.

For some applications, the computer processor is configured:

in response to the analyzing, to identify an aspect of the sensor signal selected from the group consisting of: a cardiac-related aspect of the sensor signal, and a respiration-related aspect of the sensor signal, and to identify whether the subject is in the pregnant state or the non-pregnant state, in response to the identified aspect.

For some applications:

the apparatus further includes an input unit, the identified aspect of the sensor signal is a currently-identified aspect of the sensor signal, and the computer processor is configured to identify whether the subject is in the pregnant state or the non-pregnant state by:

at least once, prior to the identification of the currently-identified aspect of the sensor signal:

receiving, via the input unit, an input that is indicative of whether the subject is pregnant, and identifying an aspect of the sensor signal at a time at which the input was received, in response to the input and the identified aspect of the sensor signal, learning a pregnancy-identification rule, and using the pregnancy-identification rule to identify whether the subject is in the pregnant state or the non-pregnant state.

For some applications:

the identified aspect of the sensor signal includes a respiratory rate of the subject, and the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

For some applications:

the identified aspect of the sensor signal includes a heart rate of the subject, and the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

For some applications:

the identified heart rate of the subject is a currently-identified heart rate, and the computer processor is further configured to identify the baseline heart rate in response to a previously-identified heart rate of the subject that was identified less than fourteen days prior to identifying the currently-identified heart rate.

There is additionally provided, in accordance with some applications of the present invention apparatus for monitoring a female subject, the apparatus including:

a sensor, configured to monitor the subject without requiring compliance of the subject, and to generate a sensor signal in response to the monitoring; and a computer processor, configured to:

receive the sensor signal, analyze the sensor signal, in response to the analyzing, automatically identify a menstrual state of the subject, and generate an output in response thereto.

For some applications, the computer processor is configured to identify the subject's menstrual state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the computer processor is configured to identify the subject's menstrual state by identifying a current menstrual state of the subject.

For some applications, the computer processor is configured to identify the subject's menstrual state by predicting an occurrence of a future menstrual state of the subject.

For some applications, the sensor is configured to be disposed upon or within a bed of the subject, and is configured to monitor the subject automatically while the subject is in her bed.

For some applications, the computer processor is configured to identify the menstrual state of the subject, using a machine-learning algorithm.

For some applications, the sensor is configured to monitor the subject without contacting the subject or clothes the subject is wearing, and without viewing the subject or clothes the subject is wearing.

For some applications, the output includes a control signal to a room-climate-regulation device, and the computer processor is configured to generate the output by communicating the control signal to the room-climate-regulation device in response to the identified menstrual state.

For some applications, the computer processor is further configured, in response to identifying the subject's menstrual state, to identify that the subject is likely to experience premenstrual syndrome (PMS) in more than 0.5 days, the computer processor being configured to generate the output in response thereto.

For some applications, the computer processor is configured to identify the menstrual state of the subject by identifying that the subject is likely to ovulate in less than 10 days.

For some applications, the computer processor is configured to identify the menstrual state of the subject by identifying that the subject is likely to ovulate in less than five days.

For some applications, the computer processor is configured to identify the menstrual state of the subject by identifying that the subject is likely to ovulate in more than 0.5 days.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to ovulate in less than 10 days by:
at least once, prior to currently receiving the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning an ovulation-prediction rule, and
using the ovulation-prediction rule to identify that the subject is likely to ovulate in less than 10 days, based upon the currently-received sensor signal.

For some applications:
the computer processor is further configured, in response to identifying the menstrual state of the subject, to identify that the subject is likely to experience premenstrual syndrome (PMS) in less than three days,
the computer processor being configured to generate the output in response thereto.

For some applications, the computer processor is configured to derive a heart rate variability (HRV) signal from the sensor signal, and to identify the subject's menstrual state, in response thereto.

For some applications:
the apparatus further includes an input unit, and
the computer processor is configured to identify that the subject is likely to experience PMS in less than three days by:
at least once, prior to currently receiving the sensor signal:
receiving, via the input unit, an input that is indicative of an occurrence of PMS of the subject, and
identifying an aspect of the sensor signal at a time at which the input was received,
in response to the input and the identified aspect of the sensor signal, learning a PMS-prediction rule, and
using the PMS-prediction rule to identify that the subject is likely to experience PMS in less than three days, based upon the currently-received sensor signal.

For some applications, the computer processor is configured:
in response to the analyzing, to identify an aspect of the sensor signal selected from the group consisting of: a cardiac-related aspect of the sensor signal, and a respiration-related aspect of the sensor signal, and
to identify the menstrual state of the subject, in response to the identified aspect.

For some applications, the identified aspect of the sensor signal includes a respiratory rate of the subject, and the computer processor is configured to identify the menstrual state of the subject by comparing the identified respiratory rate to a baseline respiratory rate.

For some applications:
the apparatus further includes an input unit,
the identified aspect of the sensor signal is a currently-identified aspect of the sensor signal, and
the computer processor is configured to identify the current phase of the menstrual cycle by:
at least once, prior to the identification of the currently-identified aspect of the sensor signal:
receiving, via the input unit, an input that is indicative of a phase of the subject's menstrual cycle, and
identifying an aspect of the sensor signal at a time at which the input was received,
in response to the input and the identified aspect of the sensor signal, learning a phase-identification rule, and
using the phase-identification rule to identify the menstrual state of the subject.

For some applications, the identified aspect of the sensor signal includes a heart rate variability (HRV) signal, the computer processor being configured to identify the menstrual state in response to the HRV signal.

For some applications, in response to the HRV signal, the computer processor is configured to identify that the current phase of the subject's menstrual cycle is a late follicular phase.

For some applications, the computer processor is configured to identify that the current phase of the subject's menstrual cycle is the late follicular phase in response to an aspect of a component of a power spectrum of the HRV signal.

For some applications, the computer processor is configured to identify that the current phase of the subject's menstrual cycle is the late follicular phase by identifying that the component of the power spectrum of the HRV signal has an amplitude that exceeds a threshold.

For some applications, the component of the power spectrum of the HRV signal lies between 0.1 and 0.5 Hz, the computer processor being configured to identify that the current phase of the subject's menstrual cycle is the late follicular phase in response to an aspect of the component of the power spectrum.

For some applications, the identified aspect of the sensor signal includes a heart rate of the subject, and the computer processor is configured to identify the menstrual state of the subject by comparing the identified heart rate to a baseline heart rate.

For some applications, the computer processor is configured, in response to the comparing, to:
ascertain that the identified heart rate is greater than the baseline heart rate; and
in response thereto, identify the menstrual state of the subject by identifying that the subject is currently within a given amount of time of ovulation of the subject.

For some applications, the computer processor is configured to identify that the subject is currently within the given amount of time of ovulation of the subject by identifying that less than the given amount of time has transpired since the subject ovulated.

For some applications, the computer processor is configured, in response to ascertaining that the identified heart rate is greater than the baseline heart rate, to identify that the subject is currently within less than two days of ovulation of the subject.

For some applications, the computer processor is configured to identify that the subject is currently within the given amount of time of ovulation of the subject in response to the identified heart rate being less than five heartbeats-per-minute greater than the baseline heart rate.

For some applications, the sensor is configured to monitor the subject during a sleeping session of the subject.

For some applications:

the computer processor is configured to analyze the sensor signal by identifying an aspect of the sensor signal that is exhibited at least two hours from a beginning of the sleeping session, and the computer processor is configured to identify the menstrual state of the subject (i) in response to the aspect of the sensor signal that is exhibited at least two hours from the beginning of the sleeping session, and (ii) substantially not in response to any aspect of the sensor signal that is exhibited less than two hours from the beginning of the sleeping session.

For some applications:

the computer processor is further configured, in response to analyzing the sensor signal, to determine a level of motion of the subject, the computer processor is configured to analyze the sensor signal by identifying an aspect of the sensor signal that is exhibited while the level of motion does not exceed a threshold, and the computer processor is configured to identify the menstrual state of the subject (i) in response to the aspect of the sensor signal that is exhibited while the level of motion does not exceed the threshold, and (ii) substantially not in response to any aspect of the sensor signal that is exhibited while the level of motion exceeds the threshold.

For some applications:

the computer processor is further configured, in response to analyzing the sensor signal, to identify a sleep stage of the subject during the sleeping session, the computer processor is configured to analyze the sensor signal by identifying an aspect of the sensor signal that is exhibited while the identified sleep stage is a particular sleep stage, and the computer processor is configured to identify the menstrual state of the subject (i) in response to the aspect of the sensor signal that is exhibited while the identified sleep stage is the particular sleep stage, and (ii) substantially not in response to any aspect of the sensor signal that is exhibited while the identified sleep stage is not the particular sleep stage.

For some applications, the particular sleep stage is a slow-wave sleep stage.

For some applications, the particular sleep stage is a rapid-eye-movement sleep stage.

For some applications, the identified aspect of the sensor signal includes a heart rate variability (HRV) signal, the computer processor being configured to identify the menstrual state of the subject in response to the HRV signal that is exhibited while the identified sleep stage is the particular sleep stage.

For some applications:

the computer processor is further configured, in response to analyzing the sensor signal, to identify an end of a chronologically-first sleep cycle of the subject during the sleeping session, the computer processor is configured to analyze the sensor signal by identifying an aspect of the sensor signal that is exhibited following the end of the chronologically-first sleep cycle, and the computer processor is configured to identify the menstrual state of the subject (i) in response to the aspect of the sensor signal that is exhibited following the end of the chronologically-first sleep cycle, and (ii) substantially not in response to any aspect of the sensor signal that is exhibited before the end of the chronologically-first sleep cycle.

For some applications:

the computer processor is further configured, in response to analyzing the sensor signal, to identify an end of a chronologically-second sleep cycle of the subject during the sleeping session, the computer processor is configured to analyze the sensor signal by identifying an aspect of the sensor signal that is exhibited following the end of the chronologically-second sleep cycle, and the computer processor is configured to identify the menstrual state of the subject (i) in response to the aspect of the sensor signal that is exhibited following the end of the chronologically-second sleep cycle, and (ii) substantially not in response to any aspect of the sensor signal that is exhibited before the end of the chronologically-second sleep cycle.

There is further provided, in accordance with some applications of the present invention, apparatus for monitoring a female subject, the apparatus including:

a sensor, configured to monitor the subject and to generate a sensor signal in response to the monitoring; and a computer processor, configured to:

receive the sensor signal, derive a cardiac-related aspect of the sensor signal by analyzing the sensor signal, based upon the derived cardiac-related aspect of the sensor signal, automatically identify whether the subject is in a pregnant state or a non-pregnant state, and generate an output in response thereto.

For some applications, the computer processor is configured to identify whether the subject is in the pregnant state or the non-pregnant state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the sensor is configured to monitor the subject without requiring compliance of the subject.

For some applications, the sensor is configured to be disposed upon or within a bed of the subject, and is configured to monitor the subject automatically while the subject is in her bed.

For some applications, the sensor is configured to monitor the subject without contacting the subject or clothes the subject is wearing, and without viewing the subject or clothes the subject is wearing.

For some applications, the output includes a control signal to a room-climate-regulation device, and the computer processor is configured to generate the output by communicating the control signal to the room-climate-regulation device in response to the identified state.

For some applications, based upon the derived cardiac-related aspect, the computer processor is configured to identify whether the subject is in the pregnant state or the non-pregnant state, using a machine-learning algorithm.

For some applications, the computer processor is configured to derive the cardiac-related aspect of the sensor signal, by deriving a heart rate of the subject, and the computer processor is configured to (i) identify that the subject is pregnant by ascertaining that a derived heart rate is not lower than a baseline heart rate, and (ii) identify that the subject is not pregnant by ascertaining that the derived heart rate is lower than the baseline heart rate.

For some applications:

the derived heart rate of the subject is a current heart rate of the subject, and the computer processor is further configured to identify the baseline heart rate in response to a previously-identified heart rate of the subject that was identified less than fourteen days prior to deriving the currently-derived heart rate.

There is additionally provided, in accordance with some applications of the present invention, apparatus for monitoring a female subject, the apparatus including:

a sensor, configured to monitor the subject without contacting the subject or clothes the subject is wearing, and without viewing the subject or clothes the subject is wearing, and to generate a sensor signal in response to the monitoring; and a computer processor, configured to:

receive the sensor signal, analyze the sensor signal, in response to the analyzing, automatically identify whether the subject is in a pregnant state or a non-pregnant state, and generate an output in response thereto.

For some applications, the computer processor is configured to identify whether the subject is in the pregnant state or the non-pregnant state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the sensor is configured to be disposed upon or within a bed of the subject, and is configured to monitor the subject automatically while the subject is in her bed.

For some applications, the output includes a control signal to a room-climate-regulation device, and the computer processor is configured to generate the output by communicating the control signal to the room-climate-regulation device in response to the identified state.

For some applications, the computer processor is configured to identify whether the subject is in the pregnant state or the non-pregnant state, using a machine-learning algorithm.

For some applications, the computer processor is configured:

in response to the analyzing, to identify an aspect of the sensor signal selected from the group consisting of: a cardiac-related aspect of the sensor signal, and a respiration-related aspect of the sensor signal, and to identify whether the subject is in the pregnant state or the non-pregnant state, in response to the identified aspect.

For some applications:

the apparatus further includes an input unit, the identified aspect of the sensor signal is a currently-identified aspect of the sensor signal, and the computer processor is configured to identify whether the subject is in the pregnant state or the non-pregnant state by:

at least once, prior to the identification of the currently-identified aspect of the sensor signal:

receiving, via the input unit, an input that is indicative of whether the subject is pregnant, and identifying an aspect of the sensor signal at a time at which the input was received, in response to the input and the identified aspect of the sensor signal, learning a pregnancy-identification rule, and using the pregnancy-identification rule to identify whether the subject is in the pregnant state or the non-pregnant state.

For some applications:

the identified aspect of the sensor signal includes a respiratory rate of the subject, and the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

For some applications:

the identified aspect of the sensor signal includes a heart rate of the subject, and the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

For some applications:

the identified heart rate of the subject is a currently-identified heart rate, and the computer processor is further configured to identify the baseline heart rate in response to a previously-identified heart rate of the subject that was identified less than fourteen days prior to identifying the currently-identified heart rate.

There is additionally provided, in accordance with some applications of the present invention, apparatus for monitoring a female subject and for use with a bed, the apparatus including:

a sensor configured to be disposed upon or within the bed, to automatically monitor the subject while the subject is in the bed, and to generate a sensor signal in response to the monitoring; and a computer processor, configured to:

receive the sensor signal, analyze the sensor signal, in response to the analyzing, automatically identify whether the subject is in a pregnant state or a non-pregnant state, and generate an output in response thereto.

For some applications, the bed includes a mattress, and the sensor is configured to be disposed underneath the mattress and to automatically monitor the subject while the subject is lying upon the mattress.

For some applications, the computer processor is configured to identify whether the subject is in the pregnant state or the non-pregnant state without determining a temperature of the subject.

For some applications, the sensor is configured not to measure a temperature of the subject.

For some applications, the sensor is configured to monitor the subject without having a direct line of sight of the subject or clothes the subject is wearing.

For some applications, the sensor is configured to monitor the subject without requiring compliance of the subject.

For some applications, the sensor is configured to monitor the subject without contacting the subject or clothes the subject is wearing, and without viewing the subject or clothes the subject is wearing.

For some applications, the output includes a control signal to a room-climate-regulation device, and the computer processor is configured to generate the output by communicating the control signal to the room-climate-regulation device in response to the identified state.

For some applications, the computer processor is configured to identify whether the subject is in the pregnant state or the non-pregnant state, using a machine-learning algorithm.

For some applications, the computer processor is configured:

in response to the analyzing, to identify an aspect of the sensor signal selected from the group consisting of: a cardiac-related aspect of the sensor signal, and a respiration-related aspect of the sensor signal, and to identify whether the subject is in the pregnant state or the non-pregnant state, in response to the identified aspect.

For some applications:

the apparatus further includes an input unit, the identified aspect of the sensor signal is a currently-identified aspect of the sensor signal, and the computer processor is configured to identify whether the subject is in the pregnant state or the non-pregnant state by:

at least once, prior to the identification of the currently-identified aspect of the sensor signal:
receiving, via the input unit, an input that is indicative of whether the subject is pregnant, and
identifying an aspect of the sensor signal at a time at which the input was received, in response to the input and the identified aspect of the sensor signal, learning a pregnancy-identification rule, and using the pregnancy-identification rule to identify whether the subject is in the pregnant state or the non-pregnant state.

For some applications:

the identified aspect of the sensor signal includes a respiratory rate of the subject, and the computer processor is configured to (i) identify that the subject is pregnant by ascertaining that the identified respiratory rate is not lower than a baseline respiratory rate, and (ii) identify that the subject is not pregnant by ascertaining that the identified respiratory rate is lower than the baseline respiratory rate.

For some applications:

the identified aspect of the sensor signal includes a heart rate of the subject, and the computer processor is configured to (i) identify that the subject is pregnant by ascertaining that the identified heart rate is not lower than a baseline heart rate, and (ii) identify that the subject is not pregnant by ascertaining that the identified heart rate is lower than the baseline heart rate.

For some applications:

the identified heart rate of the subject is a currently-identified heart rate, and the computer processor is further configured to identify the baseline heart rate in response to a previously-identified heart rate of the subject that was identified less than fourteen days prior to identifying the currently-identified heart rate.

The present invention will be more fully understood from the following detailed description of applications thereof, taken together with the drawings, in which:

DETAILED DESCRIPTION OF EMBODIMENTS

Figure 1:
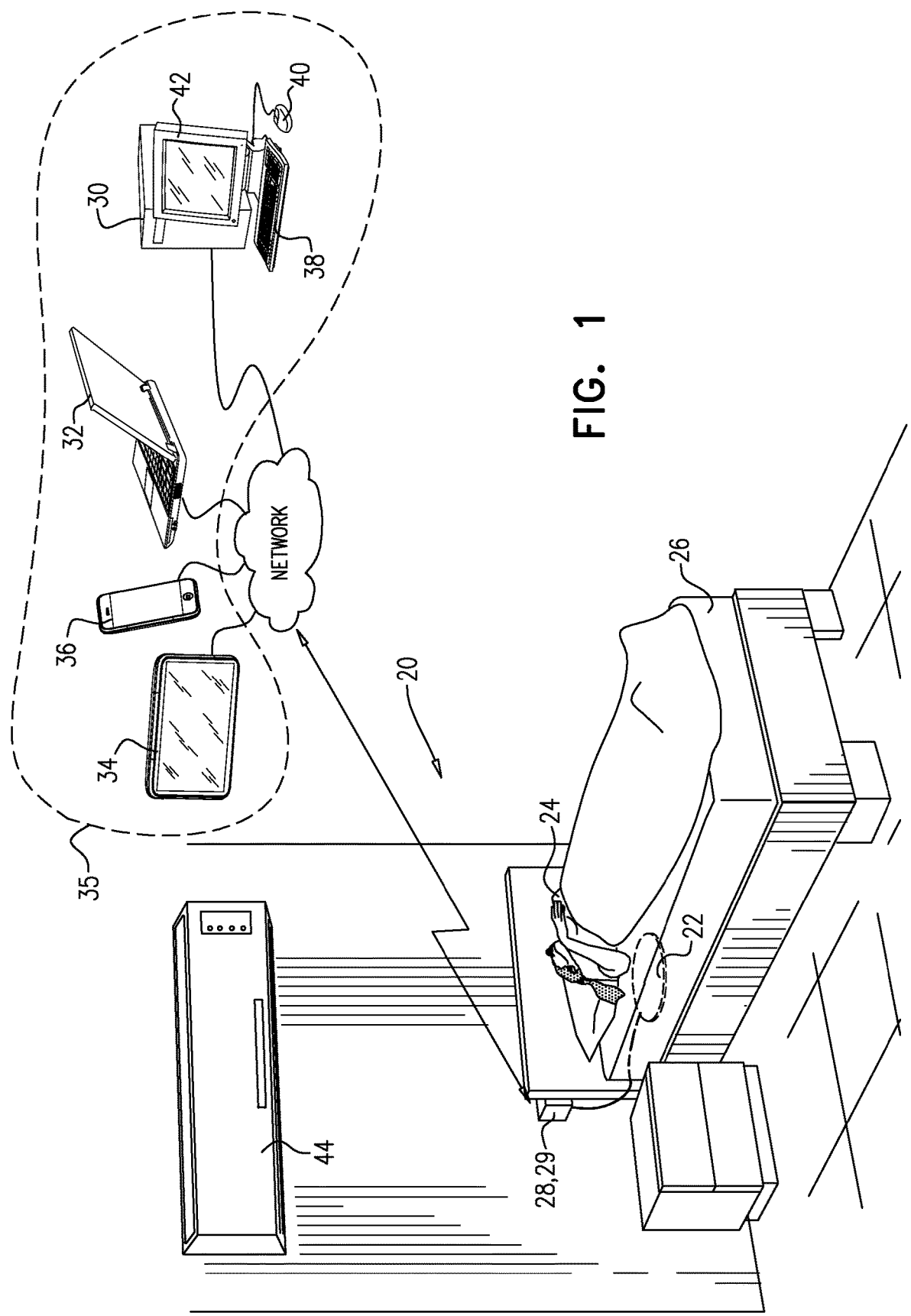
FIG. 1 is a schematic illustration of apparatus for monitoring a female subject, in accordance with some applications of the present invention.

Reference is made to FIG. 1, which is a schematic illustration of subject-monitoring apparatus 20, in accordance with some applications of the present invention. Apparatus 20 is generally used to monitor a female subject 24, while she is in her bed in a home setting.

Subject-monitoring apparatus 20 comprises a sensor 22 (e.g., a motion sensor) that is configured to monitor subject 24. Sensor 22 may be a motion sensor that is similar to sensors described in U.S. Pat. No. 8,882,684 to Halperin, which is incorporated herein by reference. The term "motion sensor" refers to a sensor that senses the subject's motion (e.g., motion due to the subject's cardiac cycle, respiratory cycle, or large-body motion of the subject), while the term "sensor" refers more generally to any type of sensor, e.g., a sensor that includes an electromyographic sensor and/or an imaging sensor.

Reference is now made to FIG. 11 of U.S. Pat. No. 8,882,684 to Halperin, which is a schematic illustration of a semi-rigid sensor plate 140 that is used as motion sensor 30, in accordance with some applications of the present invention. For some applications, the sensor is designed and/or placed under the patient's bed such as to detect only motion of the patient who is lying on the side closer to the sensor. The sensor mechanical properties are designed to collect the vibration mechanical signal only locally from the patient lying directly on top or very close to the sensor. This allows mechanical filtering of signals coming from the partner, and detection of only the signal of the patient on top of the sensor. For some applications, edges 142 of the sensor plate are hardened with respect to a central portion 144 of the sensor plate. Typically, this prevents torque from the side of the sensor plate from bending the sensor plate, and allows only direct forces generated from on top of the sensor to affect the plate such as to generate a sensor signal. In some applications, the sensor hardening on the circumference is achieved by mechanically preventing a 2-5 mm rim of the semi-rigid sensing plate from vibrating. This typically substantially reduces the signal generated by the second person as compared to that generated by the patient.

Typically, sensor 22 includes a sensor that performs monitoring of the subject without contacting the subject or clothes the subject is wearing, and/or without viewing the subject or clothes the subject is wearing. For example, the sensor may perform the monitoring without having a direct line of sight of the subject's body, or the clothes that the subject is wearing. Further typically, the sensor performs monitoring of the subject without requiring subject compliance (i.e., without the subject needing to perform an action to facilitate the monitoring that would not have otherwise been performed). It is noted that, prior to the monitoring, certain actions (such as purchasing the sensor and placing the sensor under the subject's mattress) may need to be performed. The term "without requiring subject compliance" should not be interpreted as excluding such actions. Rather the term "without requiring subject compliance" should be interpreted as meaning that, once the sensor has been purchased, placed in a suitable position and activated, the sensor can be used to monitor the subject (e.g., to monitor the subject during repeated monitoring sessions), without the subject needing to perform any actions to facilitate the monitoring that would not have otherwise been performed.

For some applications, sensor 22 is disposed on or within the subject's bed, and configured to monitor the subject automatically, while she is in her bed. For example, sensor 22 may be disposed underneath the subject's mattress 26, such that the subject is monitored while she is lying upon the mattress, and while carrying out her normal sleeping routine, without the subject needing to perform an action to facilitate the monitoring that would not have otherwise been performed.

Typically, sensor 22 is a non-temperature sensor (i.e., the sensor is not configured to measure a temperature of the subject), and the computer processor is configured to identify the subject's menstrual state and/or pregnancy state without determining a temperature of the subject.

A computer processor 28 (which acts as a control unit that performs the algorithms described herein) analyzes the signal from sensor 22. Typically, computer processor 28 communicates with a memory 29. For some applications, computer processor 28 is embodied in a desktop computer 30, a laptop computer 32, a tablet device 34, a smartphone 36, and/or a similar device that is programmed to perform the techniques described herein (e.g., by downloading a dedicated application or program to the device), such that the computer processor acts as a special-purpose computer processor. For some applications, as shown in FIG. 1, computer processor 28 is a dedicated computer processor that receives (and optionally analyzes) data from sensor 22, and communicates with computer processors of one or more of the aforementioned devices, which act as external devices.

For some applications, the subject communicates with (e.g., sends data to and/or receives data from) computer processor 28 via a user interface 35. As described, for some applications, computer processor is embodied in a desktop computer 30, a laptop computer 32, a tablet device 34, a smartphone 36, and/or a similar device that is programmed to perform the techniques described herein. For such applications, the user interface components of the device (e.g., the touchscreen, the mouse, the keyboard, the speakers, the screen) typically act as user interface 35. Alternatively, as shown in FIG. 1, computer processor 28 is a dedicated computer processor that receives (and optionally analyzes) data from sensor 22. For some such applications, the dedicated computer processor communicates with computer processors of one or more of the aforementioned external devices (e.g., via a network), and the user interfaces of the external devices (e.g., the touchscreen, the mouse, the keyboard, the speakers, the screen) are used by the subject to communicate with the dedicated computer processor and vice versa. For some applications, in order to communicate with computer processor 28, the external devices are programmed to communicate with the dedicated computer processor (e.g., by downloading a dedicated application or program to the external device).

For some applications, user interface includes an input device such as a keyboard 38, a mouse 40, a joystick (not shown), a touchscreen device (such as smartphone 36 or tablet device 34), a touchpad (not shown), a trackball (not shown), a voice-command interface (not shown), and/or other types of user interfaces that are known in the art. For some applications, the user interface includes an output device such as a display (e.g., a monitor 42, a head-up display (not shown) and/or a head-mounted display (not shown), such as Google Glass®), and/or a different type of visual, text, graphics, tactile, audio, and/or video output device, e.g., speakers, headphones, smartphone 36, or tablet device 34. For some applications, the user interface acts as both an input device and an output device. For some applications, the processor generates an output on a computer-readable medium (e.g., a non-transitory computer-readable medium), such as a disk, or a portable USB drive.

Figure 2:
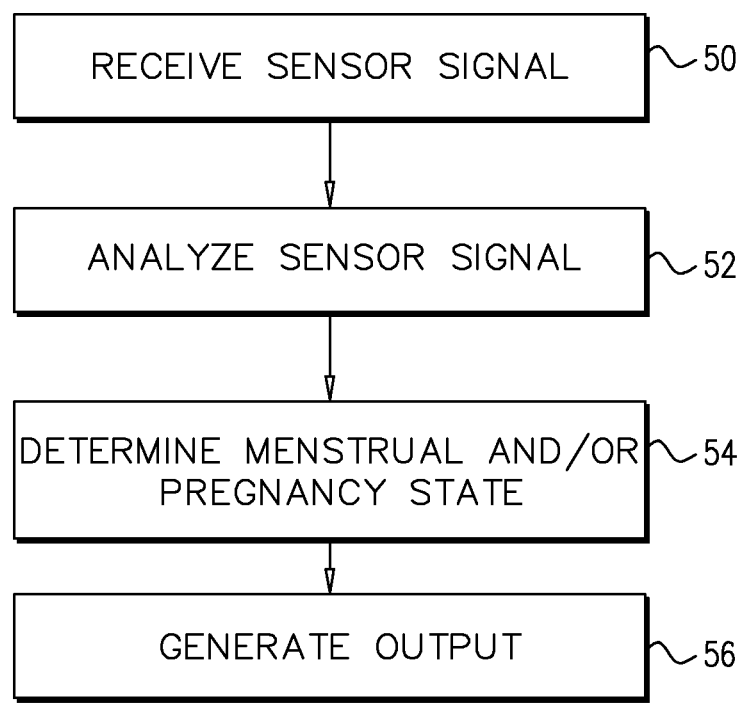
FIG. 2 is a flowchart showing steps of a method for automatically determining a menstrual state and/or a pregnancy state of the female subject, in accordance with some applications of the present invention.

Reference is now made to FIG. 2, which is a flowchart showing steps that are performed by computer processor 28, in accordance with some applications of the present invention. In a first step 50, the computer processor receives the sensor signal from sensor 22. In a second step 52, the computer processor analyzes the signal. For example, the computer processor may identify an aspect of the sensor signal, such as a cardiac-related aspect of the sensor signal, a respiration-related aspect of the sensor signal. In a third step 54, based upon the analysis of the sensor signal, the computer processor identifies a menstrual state and/or a pregnancy state (e.g., a current menstrual state and/or pregnancy state, or a predicted future state) of the subject. For example, the computer processor may (i) identify that the subject is in a pregnant state or a non-pregnant state, and/or (ii) identify a current phase of the subject's menstrual cycle, and/or (iii) identify that the subject is likely to ovulate soon.

In a fourth step 56, the computer processor generates an output in response to the identified menstrual state and/or pregnancy state. For example, the computer processor may drive an output device (e.g., as described above) to display (or otherwise output) an output that is indicative of the identified menstrual state and/or pregnancy state (for example, a smartphone application, running on smartphone 36, may be driven to display such an output). Alternatively or additionally, the processor may drive an output device (e.g., as described above) to display (or otherwise output) an output that is indicative of a recommended action to be taken by the user (e.g., "intercourse is recommended within the next 48 hours"), based upon the identified menstrual state and/or pregnancy state. Alternatively or additionally, the processor may drive a device (such as a room-climate-regulation device 44) in the subject's bedroom to perform a function or to change a parameter of its functioning in response to the identified menstrual state and/or pregnancy state, as described in further detail hereinbelow.

Figure 3:
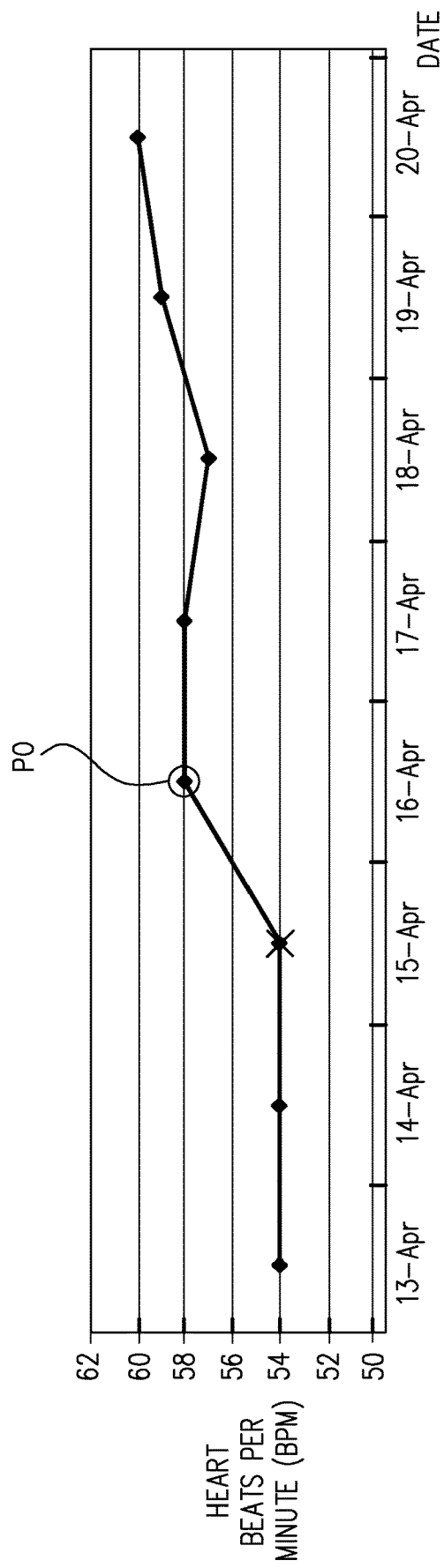
FIG. 3 is an exemplary plot of data with which the apparatus may be used, in accordance with some applications of the present invention.

Reference is now made to FIG. 3, which is an exemplary plot of data with which apparatus 20 may be used, in accordance with some applications of the present invention. In particular, the plot shows experimental data collected from a particular female subject using a non-contact sensor (i.e., a sensor that performs sensing of the subject without contacting the subject or clothes the subject is wearing). The plot shows a set of data points corresponding to the average heart rate, measured in heartbeats-per-minutes (BPM), for the subject, over a sequence of consecutive sleeping sessions. The approximate time of the subject's ovulation, as reported by the subject, is marked in the plot with an enlarged X (at 15 April). As can be seen in the plot, an increase in the average heart rate of the subject was observed post-ovulation. The plot of data thus demonstrates that, in response to observing an increased heart rate, it may be possible to identify that ovulation recently took place. In accordance with the data shown in FIG. 3, in some cases, a subject may experience an increased heart rate, and/or experience other physiological changes (e.g., a change in cardiac pattern) shortly before ovulating; thus, it may also be possible to predict an upcoming ovulation in response to observing an increased heart rate.

Based upon the above-noted observations, in some applications, step 52 of FIG. 2 is performed using the following algorithm. The subject's heart rate is identified. For example, an average heart rate over a period of time (e.g., an average heart rate over a sleeping session) may be identified. The identified heart rate is then compared to a baseline heart rate. For some applications, step 54 of FIG. 2 (determination of the subject's menstrual state and/or pregnancy state) is performed in response to the aforementioned comparison. For example, in response to ascertaining that the identified heart rate is greater than the baseline heart rate, the computer processor may identify that the subject is within a given amount of time (e.g., less than two days) of ovulation. In other words, the computer processor may identify that less than the given amount of time has transpired since the subject ovulated, or identify that it is likely that the subject will ovulate within the given amount of time. In general, this output may help the subject with her fertility planning In some applications, the computer processor uses the average heart rate of a previous sleeping session as a baseline, and in response to the identified average heart rate being greater than this baseline, the computer processor identifies the recent ovulation or predicts the upcoming ovulation.

The relatively flat portion of the plot of FIG. 3 that precedes the ovulation of the subject demonstrates that, for a subject who is generally healthy, "normal" variation in average heart rate is relatively small. Thus, even a relatively small increase in average heart rate, e.g., an increase of 1-5 heartbeats-per-minute (BPM), may be indicative of a recent or upcoming ovulation. Hence, in some applications, the computer processor identifies the recent ovulation, or predicts the upcoming ovulation, even in response to the identified heart rate being less than five heartbeats-per-minute greater than the baseline heart rate.

Typically, if the subject becomes pregnant, the heart rate of the subject remains elevated, relative to the pre-ovulation heart rate. (Although, as noted above, typically the heart rate of the subject may increase shortly before ovulation. Therefore, in this context, the "pre-ovulation heart rate" refers to the normal heart rate of the subject, prior to the increase.) If the subject does not become pregnant, on the other hand, the heart rate of the subject drops back to its pre-ovulation level. Hence, in some applications, the computer processor performs step 54 of FIG. 2, by identifying that the subject is pregnant by ascertaining that the identified heart rate is not lower than a post-ovulation baseline heart rate, the post-ovulation baseline heart rate typically being based on a previously-identified elevated heart rate. For example, with reference to FIG. 3, the post-ovulation baseline heart rate might be based on the data point labeled as PO. (For example, the post-ovulation baseline might be two BPM less than the BPM of PO, i.e., approximately 56 BPM.) If, several days after PO was observed, the average heart rate of the subject drops below this baseline, the computer processor may identify that the subject is not pregnant. Conversely, if, several days after PO was observed, the average heart rate of the subject has not dropped below this baseline, the computer processor may identify that the subject is pregnant. Alternatively or additionally, the computer processor may identify whether the subject is pregnant by comparing the current heart rate of the subject to the subject's pre-ovulation heart rate.

Typically, the post-ovulation baseline heart rate to which the average heart rate is compared is based on a previously-identified heart rate from the same menstrual cycle as the currently-identified heart rate. For example, the computer processor may identify the post-ovulation baseline heart rate in response to a heart rate of the subject that was identified less than fourteen days prior to identifying the currently-identified heart rate.

As noted above, alternatively or additionally to identifying a cardiac-related aspect of the sensor signal, the computer processor may identify a respiration-related aspect of the sensor signal, such as a respiratory rate of the subject. (For example, the computer processor may identify an average respiratory rate of the subject during a sleeping session of the subject.) In general, respiratory rate, like heart rate, typically rises to an elevated level at around the time of ovulation, and typically remains at the elevated level only if the subject becomes pregnant. Hence, the computer processor may perform step 52 of FIG. 2 as described above with respect to heart rate, but in response to the identified respiratory rate, mutatis mutandis. For example, the computer processor may identify the current phase of the menstrual cycle of the subject (e.g., the computer processor may identify that ovulation recently occurred), and/or identify whether the subject is pregnant, by comparing the identified respiratory rate to a baseline respiratory rate. The use of the respiration-related aspect of the sensor signal for step 52 of FIG. 2 may supplement, or alternatively, take the place of, the use of the cardiac-related aspect of the sensor signal.

In some applications, the identified aspect of the sensor signal includes a heart rate variability (HRV) signal, and the computer processor performs step 54 of FIG. 2 in response to the HRV signal. For example, in response to the HRV signal, the computer processor may identify that the current phase of the subject's menstrual cycle is a late follicular phase. In general, a woman's greatest chances for conceiving begin prior to ovulation, starting with the late follicular phase of her menstrual cycle. (In general, the late follicular phase begins before ovulation, sometime within five days of ovulation.) Thus, it is generally advantageous for a woman who desires to become pregnant to know that she is in her late follicular phase. In some applications, the late follicular phase is identified in response to an aspect of a component of the power spectrum of the HRV signal, e.g., in response to the component of the power spectrum of the HRV signal having an amplitude that exceeds a threshold. In some applications, the component of the power spectrum of the HRV signal that is used for identifying the late follicular phase lies between 0.1 and 0.5 Hz. Alternatively or additionally, a component that lies between 0.04 and 0.15 Hz, and/or a component that lies between 0.008 and 0.04 Hz, may be used to identify the late follicular phase. In some applications, the computer processor identifies the late follicular phase in response to a ratio of power-spectrum amplitudes; for example, the computer processor may identify the late follicular phase in response to a ratio of (i) the amplitude of a 0.04-0.15 Hz component of the spectrum, to (ii) the amplitude of a 0.008-0.04 Hz component.

In some cases, alternatively or additionally to knowing that she is in her late follicular phase, a subject may wish to know her anticipated date of ovulation. Thus, in some applications, the computer processor performs step 54 of FIG. 2, by predicting that it is likely that the subject will ovulate within a given period of time, e.g., in less than 10 days, e.g., in 0.5-5 days. As described hereinabove, the computer processor may predict the upcoming ovulation in response to an elevated heart rate of the subject. Alternatively or additionally to basing the prediction on an elevated heart rate, the computer processor may predict the upcoming ovulation in response to the HRV signal (e.g., in response to the power spectrum of the HRV signal).

For some applications, in response to determining the current stage of the subject's menstrual cycle (e.g., using techniques described herein), the computer processor generates an output indicative of when it is advisable for the subject to have intercourse such as to increase her chances of conceiving a baby. Furthermore, there is evidence that having intercourse close to ovulation or shortly thereafter (e.g., on the day of ovulation or subsequent thereto) favors conceiving a male baby, while having intercourse several days (e.g., 2-5 days) prior to ovulation favors conceiving a female baby. Therefore, for some applications, the subject (or a person related to the subject, such as the subject's partner) communicates an input to computer processor 28 (e.g., via user interface 35) that is indicative of a desire to have a child of a given gender. In response to determining the current stage of the subject's menstrual cycle (e.g., using techniques described herein), the computer processor generates an output indicative of when it is advisable for the subject to have intercourse such as to increase her chances of conceiving a baby of the desired gender.

In some applications, the computer processor identifies that the subject is likely to experience premenstrual syndrome (PMS) within a given period of time, e.g., in more than 0.5 days and/or less than three days. For example, the computer processor may predict the upcoming episode of PMS in response to the HRV signal (e.g., in response to the power spectrum of the HRV signal).

In the context of the claims and description of the present application, a phrase such as "within a given amount of time" or "within a given period of time" includes within its scope different levels of specificity. For example, for a prediction that the subject will likely ovulate within two days, the computer processor may generate a less specific output such as "You will likely ovulate within two days," or a more specific output such as "You will likely ovulate in approximately 1.5 days." Similarly, a phrase such as "in less than three days" includes within its scope different levels of specificity. For example, for a prediction that PMS will likely occur in less than three days, the computer processor may generate a less specific output such as "You will likely experience PMS in less than three days," or a more specific output such as "You will likely experience PMS in approximately two days."

Figure 4:
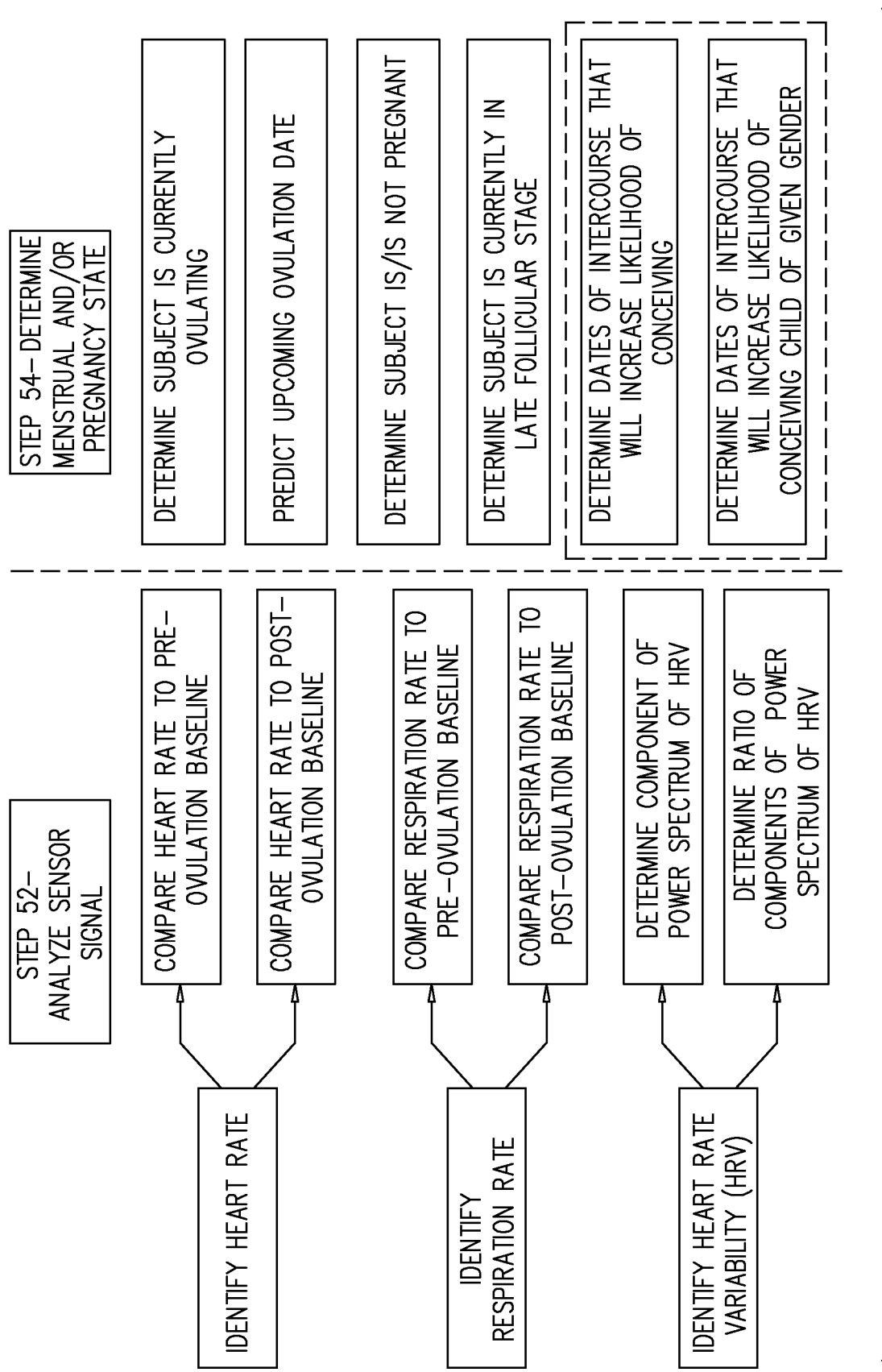
FIG. 4 is a schematic illustration showing steps of a method for automatically determining a menstrual state and/or a pregnancy state of the female subject, in accordance with some applications of the present invention.

Reference is now made to FIG. 4, which is a flowchart showing algorithms that are performed by computer processor 28, in accordance with some applications of the present invention. The left side of FIG. 4 some of the above-described algorithms, via which step 52 of FIG. 2 is performed, in accordance with some applications of the present invention. The right side of FIG. 4 shows examples of menstrual states and/or pregnancy states that are identified in step 54 of FIG. 2, and/or (inside the dashed box on the right side of FIG. 4) examples of outputs that are derived based upon the identified menstrual state and/or pregnancy state, in accordance with some applications of the present invention. It is noted the scope of the present invention is not limited to the examples shown in FIG. 4.

Figure 5:
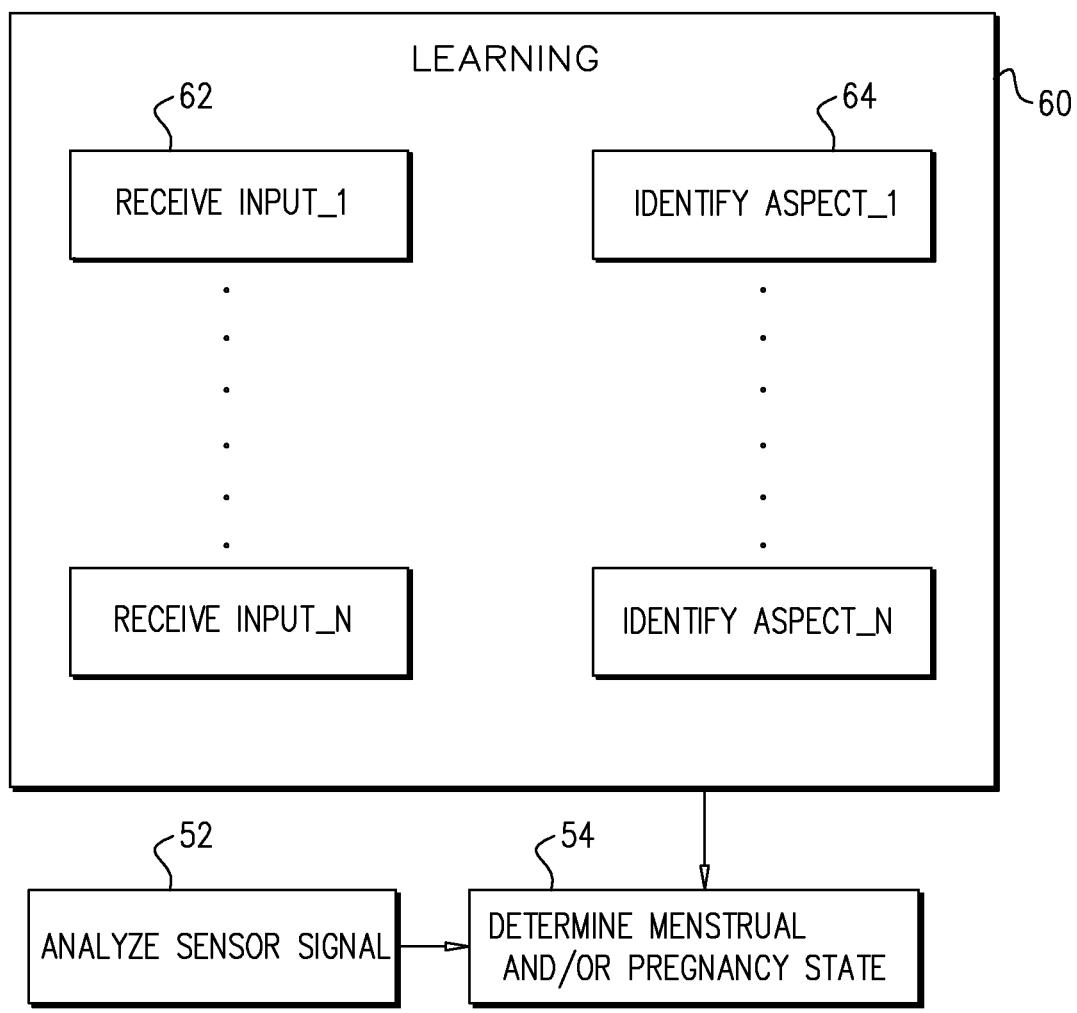
FIG. 5 is a flowchart showing steps of a method for automatically determining a menstrual state and/or a pregnancy state of the female subject that incorporate machine-learning techniques, in accordance with some applications of the present invention.

Reference is again made to FIG. 1. Reference is also made to FIG. 5, which is a flowchart showing steps of a procedure that is performed by computer processor 28, in accordance with some applications of the present invention. As described hereinabove, in some applications, apparatus 20 comprises a user interface. For some applications, at a learning step 60 (which includes a plurality of sub-steps, as described hereinbelow), computer processor 28 uses input from the user interface to learn a rule for identifying the condition of the subject. In particular, at least once (and typically more than once) prior to the identification of the currently-identified aspect of the sensor signal, the computer processor (i) receives, via the user interface, at an input-receiving step 62, an input that is indicative of the condition of the subject (e.g., the current menstrual state of the subject), and (ii) identifies an aspect of the sensor signal, at an aspect-identifying step 64. The computer processor then learns, at a rule-learning step 66, a condition-identification rule, or a condition-prediction rule, to facilitate the performance of step 54 of FIG. 2 (determining the subject's menstrual state and/or pregnancy state).

For example, FIG. 5 shows the computer processor receiving the input, and identifying the aspect of the sensor signal, a plurality of times, such that the computer processor collects a set of data points {(Aspect_i, Input_i)} for i=1 . . . N, i.e., {(Aspect_1, Input_1) . . . (Aspect_N, Input_N)}. Based at least on the plurality of data points, the computer processor implements a machine-learning algorithm to learn the rule, at rule-learning step 66. For example, the computer processor may implement a supervised learning algorithm to learn the rule. In some applications, the number of identified aspects is greater than the number of inputs (i.e., at least one "Aspect_i" does not have a corresponding "Input_i"), and the computer processor implements a semi-supervised learning algorithm to learn the rule.

In some applications, the computer processor continually improves the learned rule, based on feedback from the user. For example, if the computer processor identified that the subject was pregnant, and the identification was later found to be incorrect, the subject may report the incorrect identification to the computer processor, and the computer processor may modify the rule accordingly.

For some applications, computer processor is configured to incorporate non-subject-specific data into a machine learning-algorithm, in order to identify the subject's menstrual state and/or pregnancy state, generally in accordance with techniques described herein. For example, the computer processor may be configured to receive data (e.g., via a network) regarding measured parameters of other females, and the corresponding menstrual state(s) and/or pregnancy state(s) of those females. The computer processor is configured to use these data as additional inputs in a machine-learning algorithm, in order to identify the subject's menstrual and/or pregnancy state.

As shown in FIG. 5, for some applications, computer processor 28 performs the step of determining the subject's menstrual state and/or pregnancy state in response to the learned rule, in combination with the analysis of the sensor signal.

In general, learning step 60 may be applied to any of the menstrual state and/or pregnancy state identification applications described hereinabove, as well as to other similar applications. For example:

(i) The subject may provide one or more inputs indicative of whether she is pregnant, and the computer processor may identify the aspect of the sensor signal associated with each of the inputs. The computer processor may then learn a pregnancy-identification rule in response to the inputs and the identified aspects. The pregnancy-identification rule may then be used to identify, in response to the current sensor signal, whether the subject is pregnant.

(ii) The subject may provide one or more inputs indicative of the current phase of her menstrual cycle, and the computer processor may identify the aspect of the sensor signal associated with each of the inputs. The computer processor may then learn a phase-identification rule, and/or an ovulation-prediction rule, in response to the inputs and the identified aspects. The learned rule may then be used, in response to the current sensor signal, to identify the current phase of the subject's menstrual cycle, and/or predict an upcoming ovulation.

(iii) The subject may provide one or more inputs indicative of an occurrence of PMS, and the computer processor may identify the aspect of the sensor signal associated with each of the inputs. The computer processor may then learn a PMS-prediction rule in response to the inputs and the identified aspects. The PMS-prediction rule may then be used to predict, in response to the current sensor signal, an upcoming occurrence of PMS.

Reference is again made to FIG. 1. For some applications, computer processor 28 communicates with room-climate-regulation device 44, which may be an air-conditioning unit. For some women, changes from one phase in the menstrual cycle to another phase are accompanied by changes in climate sensitivity. Hence, in some applications, computer processor 28 performs step 56 of FIG. 2 (generating an output) by communicating a control signal to the room-climate-regulation device in response to the identified phase of the menstrual cycle. (Similarly, the computer processor may communicate the control signal in response to identifying whether the subject is pregnant.) For some applications, computer processor 28 receives an input from the subject (e.g., via user interface 35) to facilitate the control of the room-climate-regulation device. For example, the subject may define a "profile" that covers different stages of the menstrual cycle, such that each stage is mapped to an appropriate temperature setting. The computer processor then control the room-climate-regulation device based upon the defined profile, and in response to the current sensor signal.

In some applications, the computer processor is further configured, in response to analyzing the sensor signal, to identify a sleep stage of the subject during the subject's sleeping session. (To identify the sleep stage of the subject, the computer processor may utilize techniques described in U.S. 2007/0118054 to Pinhas (now abandoned), which is incorporated herein by reference.) The identification or prediction of the subject's condition is then performed in response to an aspect of the sensor signal that is exhibited while the identified sleep stage is a particular sleep stage, and substantially not in response to any aspect of the sensor signal that is exhibited while the identified sleep stage is not the particular sleep stage.

For example, the computer processor may substantially restrict the analysis to slow-wave (i.e., deep) sleep, i.e., the computer processor may identify or predict the subject's condition substantially only in response to an aspect of the sensor signal that was exhibited during slow-wave sleep. In some cases, it may be advantageous to substantially exclude REM sleep from the analysis. For example, during REM sleep, dreaming of the subject may cause changes in heart rate which, with respect to the identification of the subject's menstrual stage, constitute unwanted "noise". On the other hand, in some applications, the analysis is substantially restricted to the REM sleep stage. For example, the HRV signal during REM sleep may, in some cases, be particularly indicative of the subject's current or upcoming condition.

While the scope of the present invention includes using data from the particular sleep stage, to the complete exclusion of all other sleep stages, the scope of the present invention also includes using data from sleep stages other than the particular sleep stage, to a certain limited extent. This is indicated, in the relevant portions of the claims and description of the present application, by the word "substantially." In particular, "substantially not in response to any aspect of the sensor signal that is exhibited while the identified sleep stage is not the particular sleep stage" means that even if data that is not from the particular sleep stage is used for the analysis, this data is used to a relatively small extent, such that it does not have a significant influence on the outcome of the analysis. For example:

(i) For a non-numeric output (e.g., an output indicative of whether the subject is pregnant), or a numeric output having a relatively small number of possible values, the "substantially excluded" data might not change the outcome in more than 5% of cases. In other words, in at least 95% of cases, the computer processor would output the same value, regardless of whether the substantially excluded data is used for the analysis.

(ii) For a numeric output having a relatively large number of possible values (e.g., an output that is generally continuous-valued, such as an expected amount of time until ovulation), the substantially excluded data might not change the value of the output by more than 5%. For example, if, when completely excluding the data, a value of 2.0 days were output, including the data in the analysis would not change the output by more than 0.1 days.

It is noted that the scope of the present invention includes restricting the analysis to more than one sleep stage. For example, the analysis may be restricted to all sleep stages except for REM sleep.

In some applications, in response to analyzing the sensor signal, the computer processor identifies the end of the chronologically-first or chronologically-second sleep cycle of the subject during the sleeping session. (For example, to identify the end of a sleep cycle, the computer processor may utilize techniques described above with respect to sleep-stage identification.) In such applications, alternatively or additionally to substantially restricting the analysis to a particular sleep stage, the computer processor may substantially restrict the analysis to data collected after the end of the chronologically-first or chronologically-second sleep cycle. (In this context, as before, the word "substantially" is to be understood to indicate that the computer processor does not necessarily completely exclude from the analysis data that is collected outside the specified portion of the sleeping session.) The inventors have observed that in some cases, data collected during the first and/or second sleep cycle may contain "artifacts," i.e., the data may reflect activities (e.g., eating) that the subject performed before going to sleep, and may thus "mislead" the computer processor. Hence, by substantially excluding the first and/or second sleep cycle from the analysis, these artifacts are substantially filtered out. Alternatively or additionally, the computer processor may substantially restrict the analysis to data collected at least a particular amount of time from the beginning of the sleeping session. For example, the computer processor may substantially exclude from the analysis any data that is collected less than two hours from the beginning of the sleeping session.

Alternatively or additionally to the above, in some applications, the computer processor may, in response to analyzing the sensor signal, determine a level of motion of the subject while the subject sleeps. In such applications, the computer processor may substantially restrict the analysis to data collected while the level of motion does not exceed a threshold. (Again, the word "substantially" is to be understood as explained above.) In this manner, motion artifacts in the sensor signal are substantially excluded from the analysis.

The scope of the present invention includes "substantial exclusion" of the first or second sleep cycle of the subject in any relevant context. In other words, the computer processor may identify or predict any physiological condition (i) in response to an aspect of the sensor signal that is exhibited following the end of the chronologically-first or chronologically-second sleep cycle, and (ii) substantially not in response to any aspect of the sensor signal that is exhibited before the end of the chronologically-first or chronologically-second sleep cycle. Furthermore, the analysis in which the first and/or second sleep cycle are excluded may be in response to a signal from any type of sensor, including those sensors that require compliance of the subject to monitor the subject.

In general, computer processor 28 may be embodied as a single computer processor 28, or a cooperatively networked or clustered set of computer processors. Computer processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, computer processor 28 is connected to one or more sensors via one or more wired or wireless connections. Computer processor 28 is typically configured to receive signals (e.g., motion signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that each block of the flowcharts shown in FIGS. 2, 4, and 5 and combinations of blocks in the flowcharts, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 2, 4, and 5, computer processor 28 typically acts as a special purpose menstrual-state and/or pregnancy-state identification computer processor. Typically, the operations described herein that are performed by computer processor 28 transform the physical state of memory 29, which is a real physical article, to have a different magnetic polarity, electrical charge, or the like depending on the technology of the memory that is used.

Techniques described herein may be practiced in combination with techniques described in one or more of the following patents and patent applications, which are incorporated herein by reference. In some applications, techniques and apparatus described in one or more of the following applications are combined with techniques and apparatus described herein:

U.S. patent application Ser. No. 11/048,100, filed Jan. 31, 2005, which issued as U.S. Pat. No. 7,077,810;

U.S. patent application Ser. No. 11/197,786, filed Aug. 3, 2005, which issued as U.S. Pat. No. 7,314,451;

U.S. patent application Ser. No. 11/446,281, filed Jun. 2, 2006, which issued as U.S. Pat. No. 8,376,954;

U.S. patent application Ser. No. 11/552,872, filed Oct. 25, 2006, now abandoned, which published as U.S. 2007/0118054;

U.S. patent application Ser. No. 11/755,066, filed May 30, 2007, now abandoned, which published as U.S. 2008/0114260;

U.S. patent application Ser. No. 11/782,750, filed Jul. 25, 2007, which issued as U.S. Pat. No. 8,403,865;

U.S. patent application Ser. No. 12/113,680, filed May 1, 2008, which published as U.S. 2008/0275349;

U.S. patent application Ser. No. 12/842,634, filed Jul. 23, 2010, which issued as U.S. Pat. No. 8,517,953;

U.S. patent application Ser. No. 12/938,421, filed Nov. 3, 2010, which issued as U.S. Pat. No. 8,585,607;

U.S. patent application Ser. No. 12/991,749, filed Nov. 9, 2010, which published as U.S. 2011/0112442;

U.S. patent application Ser. No. 13/107,772, filed May 13, 2011, which issued as U.S. Pat. No. 8,491,492;

U.S. patent application Ser. No. 13/305,618, filed Nov. 28, 2011, which published as U.S. 2012/0132211;

U.S. patent application Ser. No. 13/389,200, filed Jun. 13, 2012, now abandoned, which published as U.S. 2012/0253142;

U.S. patent application Ser. No. 13/750,957, filed Jan. 25, 2013, which issued as U.S. Pat. No. 8,603,010

U.S. patent application Ser. No. 13/750,962, filed Jan. 25, 2013, which issued as U.S. Pat. No. 8,679,034;

U.S. patent application Ser. No. 13/863,293, filed Mar. 15, 2013, now abandoned, which published as U.S. 2013/0245502;

U.S. patent application Ser. No. 13/906,325, filed May 30, 2013, which issued as U.S. Pat. No. 8,882,684;

U.S. patent application Ser. No. 13/921,915, filed Jun. 19, 2013, which issued as U.S. Pat. No. 8,679,030;

U.S. patent application Ser. No. 14/019,371, filed Sep. 5, 2013, which published as U.S. 2014/0005502;

U.S. patent application Ser. No. 14/020,574, filed Sep. 6, 2013, which issued as U.S. Pat. No. 8,731,646;

U.S. patent application Ser. No. 14/054,280, filed Oct. 15, 2013, which issued as U.S. Pat. No. 8,734,360;

U.S. patent application Ser. No. 14/150,115, filed Jan. 8, 2014, which issued as U.S. Pat. No. 8,840,564;

U.S. patent application Ser. No. 14/231,855, filed Apr. 1, 2014, which issued as U.S. Pat. No. 8,992,434;

U.S. patent application Ser. No. 14/458,399, filed Aug. 13, 2014, which issued as U.S. Pat. No. 8,998,830;

U.S. patent application Ser. No. 14/474,357, filed Sep. 2, 2014, which published as U.S. 2014/0371635;

International Patent Application PCT/IL2005/000113, which published as WO 2005/074361;

International Patent Application PCT/IL2006/000727, which published as WO 2006/137067;

International Patent Application PCT/IB2006/002998, which published as WO 2007/052108;

International Patent Application PCT/IL2008/000601, which published as WO 2008/135985;

International Patent Application PCT/IL2009/000473, which published as WO 2009/138976;

International Patent Application PCT/IL2011/050045, which published as WO 2012/077113; and International Patent Application PCT/IL2013/050283, which published as WO 2013/150523.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A monitoring apparatus for monitoring a female subject, during a sleeping session, the monitoring apparatus comprising:

a sensor configured to monitor the subject and to generate a sensor signal in response to the monitoring, the sensor comprising a semi-rigid sensor plate having edges that are hardened with respect to a central portion of the sensor plate, the hardened edges configured to allow only direct forces generated from on top of the sensor to affect the sensor plate such as to generate the sensor signal; and a computer processor, configured:

to receive the sensor signal, to derive from the sensor signal data related to one or more physiological parameters of the subject during the sleeping session, using the derived data, to identify sleep stages of the subject during the subject's sleeping session, to identify a menstrual state of the subject, in response to (A) comparing over a plurality of sleeping sessions (i) the one or more physiological parameters exhibited while an identified sleep stage is a particular sleep stage to (ii) respective baseline values of the one or more physiological parameters, and substantially not in response to (B) physiological parameters exhibited while an identified sleep stage is not the particular sleep stage, and to generate an output to the subject indicating her menstrual state in response to the identified menstrual state of the subject.

2. The monitoring apparatus according to claim 1, wherein the computer processor is configured to identify the subject's menstrual state without determining a temperature of the subject.

3. The monitoring apparatus according to claim 1, wherein the computer processor is configured to generate the output in response to the identified menstrual state of the subject, by generating an output that is indicative of a menstrual state of the subject that is currently occurring.

4. The monitoring apparatus according to claim 1, wherein the computer processor is configured to generate the output in response to the identified menstrual state of the subject, by generating an output that is indicative of a predicted occurrence of a future menstrual state of the subject.

5. The monitoring apparatus according to claim 1, wherein the computer processor is configured to identify the menstrual state of the subject, using a machine-learning algorithm.

6. The monitoring apparatus according to claim 1, wherein the computer processor is configured to generate the output in response to the identified menstrual state of the subject, by generating an output indicating that the subject is likely to ovulate within a given time period that is less than 10 days.

7. The monitoring apparatus according to claim 1,
wherein the computer processor is configured to generate the output in response to the identified menstrual state of the subject, by generating an output indicating that the subject is likely to experience premenstrual syndrome (PMS) within a given time period that is less than three days.

8. The monitoring apparatus according to claim 1, wherein the computer processor is configured:
to derive the data related to the one or more physiological parameters of the subject during the sleeping session, by deriving data related to one or more physiological parameters of the subject selected from the group consisting of: a cardiac-related physiological parameter, and a respiration-related physiological parameter.

9. The monitoring apparatus according to claim 1, wherein:
the computer processor is configured to identify sleep stages of the subject during the subject's sleeping session by using the derived data to identify when the subject is undergoing slow-wave sleep, and when the subject is not undergoing slow-wave sleep, during the subject's sleeping session; and
the computer processor is configured to identify the menstrual state of the subject,
in response to
(A) comparing over the plurality of sleeping sessions
(i) the one or more physiological parameters exhibited while the subject is undergoing slow-wave sleep to (ii) the respective baseline values of the one or more physiological parameters
and substantially not in response to
(B) physiological parameters exhibited while the subject is not undergoing slow-wave sleep.

10. The monitoring apparatus according to claim 1, wherein:
the computer processor is configured to identify sleep stages of the subject during the subject's sleeping session by using the derived data to identify when the subject is undergoing REM sleep, and when the subject is not undergoing REM sleep, during the subject's sleeping session; and
the computer processor is configured to identify the menstrual state of the subject,
in response to
(A) comparing over the plurality of sleeping sessions
(i) the one or more physiological parameters exhibited while the subject is undergoing REM sleep to (ii) the respective baseline values of the one or more physiological parameters,
and substantially not in response to
(B) physiological parameters exhibited while the subject is not undergoing REM sleep.

11. The monitoring apparatus according to claim 1, wherein:
the computer processor is configured to identify sleep stages of the subject during the subject's sleeping session by using the derived data to identify when the subject is undergoing REM sleep, and when the subject is not undergoing REM sleep, during the subject's sleeping session; and
the computer processor is configured to identify the menstrual state of the subject,
in response to
(A) comparing over the plurality of sleeping sessions
(i) the one or more physiological parameters exhibited while the subject is not undergoing REM sleep to (ii) the respective baseline values of the one or more physiological parameters,
and substantially not in response to
(B) physiological parameters exhibited while the subject is undergoing REM sleep.

12. A monitoring apparatus for monitoring a female subject, during a sleeping session, the monitoring apparatus comprising:
a sensor configured to monitor the subject and to generate a sensor signal in response to the monitoring,
the sensor comprising a semi-rigid sensor plate having edges that are hardened with respect to a central portion of the sensor plate, the hardened edges configured to allow only direct forces generated from on top of the sensor to affect the sensor plate such as to generate a sensor signal; and
a computer processor, configured:
to receive the sensor signal,
to derive from the sensor signal data related to one or more physiological parameters of the subject selected from the group consisting of: a cardiac-related physiological parameter of the subject during the sleeping session, and a respiration-related physiological parameter of the subject during the sleeping session,
using the derived data, to identify sleep stages of the subject during the subject's sleeping session,
to identify a menstrual state of the subject,
in response to
(A) comparing over a plurality of sleeping sessions
(i) the one or more physiological parameters exhibited while an identified sleep stage is a particular sleep stage to (ii) respective baseline values of the one or more physiological parameters,
and substantially not in response to
(B) physiological parameters exhibited while an identified sleep stage is not the particular sleep stage, and
to generate an output in response to the identified menstrual state of the subject.

13. The monitoring apparatus according to claim 12, wherein the computer processor is configured to identify the subject's menstrual state without determining a temperature of the subject.

14. The monitoring apparatus according to claim 12, wherein the computer processor is configured to generate the output in response to the identified menstrual state of the subject, by generating an output that is indicative of a menstrual state of the subject that is currently occurring.

15. The monitoring apparatus according to claim 12, wherein the computer processor is configured to generate the output in response to the identified menstrual state of the subject, by generating an output that is indicative of a predicted occurrence of a future menstrual state of the subject.

16. The monitoring apparatus according to claim 12, wherein the computer processor is configured to identify the menstrual state of the subject, using a machine-learning algorithm.

17. The monitoring apparatus according to claim 12, wherein the computer processor is configured to generate the output in response to the identified menstrual state of the subject, by generating an output indicating that the subject is likely to ovulate within a given time period that is less than 10 days.

18. The monitoring apparatus according to claim 12,
wherein the computer processor is configured to generate the output in response to the identified menstrual state of the subject, by generating an output indicating that the subject is likely to experience premenstrual syndrome (PMS) within a given time period that is less than three days.

19. The monitoring apparatus according to claim 12, wherein the selected physiological parameter is the cardiac-related physiological parameter of the subject during the sleeping session, and the computer processor is configured to derive the data related to the cardiac-related physiological parameter of the subject during the sleeping session by deriving data related to heart rate variability (HRV) of the subject during the sleeping session.

20. The monitoring apparatus according to claim 12, wherein:
the computer processor is configured to identify sleep stages of the subject during the subject's sleeping session by using the derived data to identify when the subject is undergoing slow-wave sleep, and when the subject is not undergoing slow-wave sleep, during the subject's sleeping session; and
the computer processor is configured to identify the menstrual state of the subject,
in response to
(A) comparing over the plurality of sleeping sessions
(i) the one or more physiological parameters exhibited while the subject is undergoing slow-wave sleep to (ii) the respective baseline values of the one or more physiological parameters,
and substantially not in response to
(B) physiological parameters exhibited while the subject is not undergoing slow-wave sleep.

21. The monitoring apparatus according to claim 12, wherein:
the computer processor is configured to identify sleep stages of the subject during the subject's sleeping session by using the derived data to identify when the subject is undergoing REM sleep, and when the subject is not undergoing REM sleep, during the subject's sleeping session; and
the computer processor is configured to identify the menstrual state of the subject,
in response to
(A) comparing over the plurality of sleeping sessions
(i) the one or more physiological parameters exhibited while the subject is undergoing REM sleep to (ii) the respective baseline values of the one or more physiological parameters,
and substantially not in response to
(B) physiological parameters exhibited while the subject is not undergoing REM sleep.

22. The monitoring apparatus according to claim 12, wherein:
the computer processor is configured to identify sleep stages of the subject during the subject's sleeping session by using the derived data to identify when the subject is undergoing REM sleep, and when the subject is not undergoing REM sleep, during the subject's sleeping session; and
the computer processor is configured to identify the menstrual state of the subject,
in response to
(A) comparing over the plurality of sleeping sessions
(i) the one or more physiological parameters exhibited while the subject is not undergoing REM sleep to (ii) the respective baseline values of the one or more physiological parameters,
and substantially not in response to
(B) physiological parameters exhibited while the subject is undergoing REM sleep.

23. The monitoring apparatus according to claim 12, wherein:
the selected one or more physiological parameters are the cardiac-related physiological parameter of the subject during the sleeping session and the respiration-related physiological parameter of the subject during the sleeping session, and
the computer processor is configured to:
identify the menstrual state of the subject in response to
(A) comparing over a plurality of sleeping sessions (i) the cardiac-related physiological parameter exhibited while the identified sleep stage is the particular sleep stage and the respiration-related physiological parameter exhibited while the identified sleep stage is the particular sleep stage to (ii) respective baseline values of the cardiac-related physiological parameter and the respiration-related physiological parameter,
and substantially not in response to
(B) physiological parameters exhibited while an identified sleep stage is not the particular sleep stage.

* * * * *